United States Patent [19]

Minai et al.

[11] Patent Number: 5,534,188

[45] Date of Patent: Jul. 9, 1996

[54] ACETYLENE DERIVATIVES, PROCESS FOR PRODUCING THE SAME, LIQUID CRYSTAL COMPOSITION CONTAINING THE SAME AS AN ACTIVE INGREDIENT, AND LIQUID CRYSTAL ELEMENT USING SAID LIQUID CRYSTAL COMPOSITION

[75] Inventors: Masayoshi Minai, Moriyama; Takayuki Higashii, Takatsuki; Shoji Toda, Takatsuki; Naoyuki Takano, Takatsuki; Kayoko Ueda; Koichi Fujisawa, both of Tsukuba, all of Japan

[73] Assignee: Sumitomo Chemical Company, Limited, Osaka, Japan

[21] Appl. No.: 256,051

[22] PCT Filed: Oct. 26, 1993

[86] PCT No.: PCT/JP93/01544

§ 371 Date: Jun. 24, 1994

§ 102(e) Date: Jun. 24, 1994

[87] PCT Pub. No.: WO94/10116

PCT Pub. Date: May 11, 1994

[30] Foreign Application Priority Data

Oct. 26, 1992 [JP] Japan ................................. 4-287375
Dec. 3, 1992 [JP] Japan ................................. 4-324477
Dec. 22, 1992 [JP] Japan ................................. 4-342050

[51] Int. Cl.[6] ............................ C09K 19/12; C09K 19/30; C07D 239/02; C07D 213/62
[52] U.S. Cl. ................. 252/299.61; 560/100; 560/113; 560/122; 560/123; 560/124; 560/129; 560/187; 560/219; 560/221; 560/228; 568/643; 568/659; 252/299.66; 544/224; 544/238; 544/239; 544/296; 544/295; 544/316; 544/318; 544/319; 544/333; 544/336; 544/405; 544/408; 546/258; 546/257; 546/301; 546/302; 546/342; 546/339
[58] Field of Search .................................. 544/408, 333, 544/238, 239, 224, 405, 298, 335, 357; 546/257, 301; 560/221; 568/643; 252/299.61, 299.66

[56] References Cited

U.S. PATENT DOCUMENTS

| | | | |
|---|---|---|---|
| 4,299,844 | 11/1981 | Goudie | 424/308 |
| 4,834,904 | 5/1989 | Krause et al. | 252/299.01 |
| 5,047,172 | 10/1991 | Saito et al. | 252/299.61 |
| 5,167,859 | 12/1992 | Wachtler et al. | 252/299.61 |
| 5,326,497 | 7/1994 | Buchecker et al. | 252/299.61 |
| 5,366,657 | 11/1994 | Illian et al. | 252/299.6 |

FOREIGN PATENT DOCUMENTS

| | | |
|---|---|---|
| 0435632 | 7/1991 | European Pat. Off. . |
| 0535635 | 4/1993 | European Pat. Off. . |
| 52-137456 | 11/1977 | Japan . |
| 2275864 | 11/1990 | Japan . |
| 4178369 | 6/1992 | Japan . |
| 578272 | 3/1993 | Japan . |
| 1538473 | 1/1979 | United Kingdom . |

OTHER PUBLICATIONS

Dieck, H. A. et al. *J. Organomet. Chem.* 93, 259–263 (1975).
CHEMICAL ABSTRACTS, vol. 113, No. 12, 17 Sep. 1990, Columbus, Ohio, US; abstract no. 106585, SUGAWARA S, "Optically active diphenylacetylene derivatives and liquid-crystal compositions containing them" & JP-A-89 301 639 (NIPPON TELEGRAPH AND TELEPHONE CORP., JAPAN), 5 Dec. 1989.

*Primary Examiner*—Cecila Tsang
*Assistant Examiner*—King Lit Wong
*Attorney, Agent, or Firm*—Watson Cole Stevens Davis

[57] ABSTRACT

An acetylene derivative represented by general formula (I):

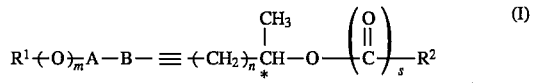

wherein $R^1$ is saturated or unsaturated alkyl group having 3–20 carbon atoms, $R^2$ is saturated or unsaturated alkyl group having 1–20 carbon atoms which may optionally be substituted by halogen atom or alkoxyalkyl group having 2–20 carbon atoms, A and B represent phenylene group or the like or taken as —A—B— represent naphthalene group or the like, m and s are each 0 or 1, n is integer of 1–6, and * means asymmetric carbon atom; a process for producing said acetylene derivative, a liquid crystal composition using the same as active ingredient, and a liquid crystal element using said composition.

3 Claims, No Drawings

ACETYLENE DERIVATIVES, PROCESS FOR PRODUCING THE SAME, LIQUID CRYSTAL COMPOSITION CONTAINING THE SAME AS AN ACTIVE INGREDIENT, AND LIQUID CRYSTAL ELEMENT USING SAID LIQUID CRYSTAL COMPOSITION

TECHNICAL FIELD

1. Background Technique

This invention relates to acetylene derivatives useful as an ingredient of ferroelectric liquid crystal compositions, a process for producing the same, compounds obtainable from the acetylene derivatives and a process for producing said compounds, liquid crystal compositions containing said compounds as active ingredient, and liquid crystal elements using said liquid crystal compositions.

2. Background Technique

At the present time, TN (twisted nematic) type displaying methods are most widely employed in the field of liquid crystal elements. TN liquid crystal elements have many merits such as lowness in driving voltage, smallness in consumption of electric power, etc. In the point of response speed, however, the TN liquid crystal elements are inferior to luminescence type display elements such as cathode tube, electroluminescence, plasma display and the like. Although a new TN type display element in which the angle of twist is altered to 180° to 270° has been developed, it is still insufficient in response speed. In spite of such endeavors for improvement as the above, a TN type display element having a high response speed is not yet realized. However, there is a possibility of marked improvement in response speed in the new displaying method using a ferroelectric liquid crystal which is energetically being studied in the recent time (Clark et al.; Applied. Phys. Lett., 36, 899 (1980)). This method uses a chiral smectic phase exhibiting a ferroelectricity such as chiral smectic C phase (hereinafter, abbreviated to Sc*), etc. It is known that the phase exhibiting a ferroelectricity is not limited to Sc* phase, but chiral smectic F, G, H and I phases and the like also exhibit a ferroelectricity.

Ferroelectric liquid crystal materials used in practical ferroelectric liquied crystal elements are required to have many characteristic properties. At the present stage, such requirements cannot fully be satisfied by a single compound, but a ferroelectric liquid crystal composition obtained by mixing together a number of liquid crystal compounds or (non-liquid crystal) compounds must be used for satisfying such requirements.

A ferroelectric liquid crystal composition can be obtained not only by using a composition composed of ferroelectric liquid crystal compounds alone. Thus, it has been reported in JP-A-61-195187 that a ferroelectric liquid crystal composition, as a whole, can be obtained by using a compound and composition showing non-chiral smectic C, F, G, H, I phases, etc. (hereinafter, abbreviated to Sc phase, etc.) as a fundamental substance and mixing thereinto one or more compounds showing ferroelectric liquid crystal phase. Further, in another paper (Mol. Cryst. Liq. Cryst., 89, 327 (1982)), it has been reported that a ferroelectric liquid crystal composition, as a whole, can be obtained by using a compound and composition showing the Sc phase, etc. as a fundamental material and mixing thereinto one or more compounds which are optically active and show no ferroelectric liquid crystal phase.

Considering these facts collectively, it can be understood that a ferroelectric liquid crystal composition can be constituted by using one or more optically active substances as fundamental material, whether these compounds show ferroelectric liquid crystal phase or not. However, it is desirable that the optically active substance shows a liquid crystal phase and, even if the optically active substance does not show liquid crystal phase, it is a pseudo liquid crystal substance or a substance of which structure resembles that of liquid crystal compound. However, up to today, there has been discovered no liquid crystal material having a spontaneous polarization necessary for a high-speed response, having a low viscosity and showing ferroelectric liquid crystal phase in a sufficiently broad temperature range involving the ambient temperature range.

As a known paper having a relation with this invention, JP-A-4-141969 can be referred to, wherein are disclosed olefin-type liquid crystal compounds and phenylpyrimidine-type compounds obtained by reduction thereof. However, the olefin-type compounds are not satisfactory from the viewpoint of long-term use because they are readily isomerizable or polymerizable by light or heat. Further, since these olefin compounds are produced by Heck reaction, their condensation products can be contaminated by isomers, and production of a high-purity product requires complicated purifying processes such as chromatography, recrystallization, etc. which makes the process unsatisfactory from industrial point of view.

DISCLOSURE OF THE INVENTION

It is an object of this invention to provide a compound solving the above-mentioned problems advantageously from industrial point of view.

In view of the above, the present inventors have studied a process free from the above-mentioned problems. As a result, it has been found that the object can be achieved in very high purity and yield by using an acetylene derivative, and that a compound obtainable by reducing such acetylene derivative also has a very high purity. Based on these findings, this invention has been accomplished.

Such acetylene derivative is higher in the temperature region of liquid phase exhibition and great in spontaneous polarization, and therefore it is useful as a liquid crystal additive.

Thus, this invention relates to an acetylene derivative represented by general formula (I):

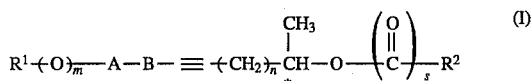

wherein $R^1$ represents saturated or unsaturated alkyl group having 3–20 carbon atoms, $R^2$ represents $C_{1-20}$ saturated or unsaturated alkyl group optionally substituted by halogen atom or $C_{2-20}$ alkoxyalkyl group, A and B each represents:

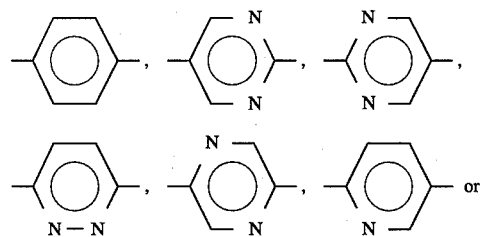

-continued

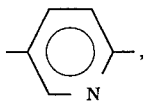

or A—B, taken conjointly, represents:

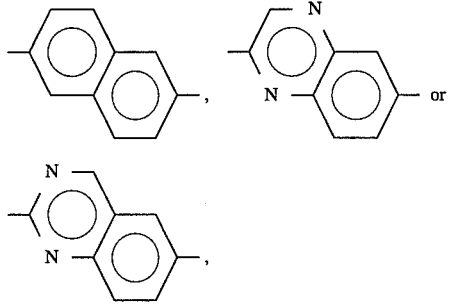

m and s each represents 0 or 1, n represents an integer of 0–6, and the mark * signifies an asymmetric carbon atom; a process for producing said acetylene derivative (I); a compound represented by general formula (II) which is obtainable by reducing the acetylene derivative:

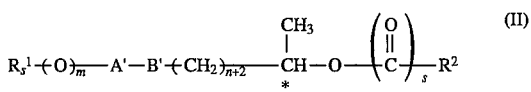

wherein $R_S^1$ represents alkyl group having 3–20 carbon atoms, $R^2$ represents $C_{1-20}$ saturated or unsubstituted alkyl group optionally substituted by halogen atom or $C_{2-20}$ alkoxyalkyl group, A' and B' each represents:

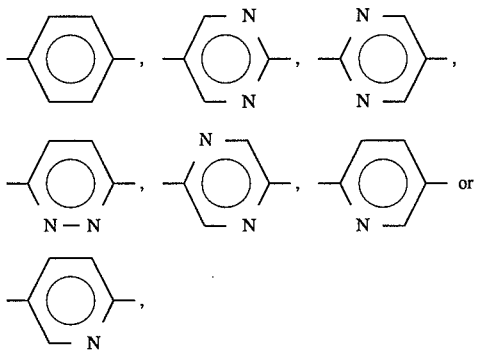

or A'—B' taken conjointly, represents:

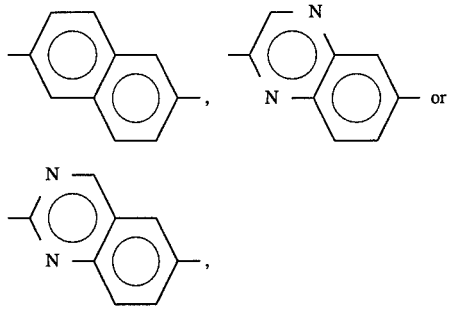

m and s each represents 0 or 1, n represents an integer of 0–6, and the mark * signifies an asymmetric carbon atom, provided that

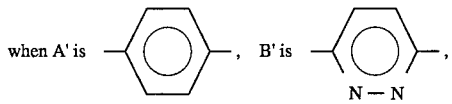

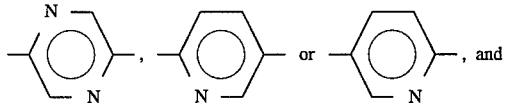

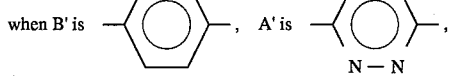

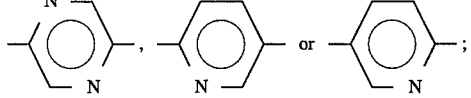

a process for producing a compound of the formula (II); a liquid crystal composition containing one of those compounds as an active ingredient; and a liquid crystal element using said liquid crystal composition.

BEST EMBODIMENT FOR PRACTICE OF THE INVENTION

Next, this invention is detailed.

The acetylene derivative (I) of this invention wherein s is 1 can be obtained by reacting an alcohol derivative represented by general formula (III):

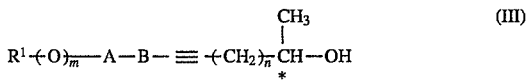

wherein $R^1$, A, B, m, n and the mark * are as defined above, with a carboxylic acid represented by the following general formula:

$R^2COR'$ 

wherein $R^2$ is as defined above and R' represents hydroxyl group, $OCOR^2$ or halogen atom.

In the above-mentioned reaction between alcohol derivative (III) and carboxylic acid, the carboxylic acids which can be used include carboxylic acids having an alkyl group represented by $R^2$, acid anhydrides thereof and acid halides thereof such as acid chloride and acid bromide. These carboxylic acids may be any of racemic mixture and optically active compound.

The above-mentioned reaction is usually carried out in the presence or absence of solvent, generally in the presence of a catalyst.

When a solvent is used in the reaction, the solvents which can be used include single members and mixtures thereof of the solvents inert to the reaction such as ethers, ketones, aliphatic and aromatic hydrocarbons, halogenated hydrocarbons, aprotic polar solvents and the like, of which examples include tetrahydrofuran, ethyl ether, acetone, methyl ethyl ketone, toluene, benzene, chlorobenzene, dichloromethane, dichlorethane, chloroform, carbon tetrachloride, dimethylformamide, hexane and the like. The quantity of the solvent is not particularly limited.

When an acid anhydride or acid halide of aliphatic carboxylic acid is used in the reaction, its quantity must not be smaller than one equivalent per equivalent of alcohol derivative (III). Although upper limit of its quantity is not particularly limited, the upper limit is preferably 1.1–4 equivalents per equivalent of (III).

As the catalyst, organic and inorganic basic substances such as dimethylaminopyridine, 4-pyrrolidinopyridine, triethylamine, tri-n-butylamine, pyridine, picoline, collidine, imidazole, sodium carbonate, sodium methoxide, potassium hydrogen carbonate and the like can be referred to.

Organic acids or inorganic acids such as toluenesulfonic acid, methanesulfonic acid, sulfuric acid and the like are also usable as the catalyst.

Among these catalysts, pyridine and triethylamine are particularly preferred when an acid halide of carboxylic acid is used as the starting material.

The quantity of the catalyst varies depending on the combination of acid anhydride or acid halide of carboxylic acid and catalyst, and cannot always be specified. When an acid halide is used, the quantity of catalyst is at least one equivalent per equivalent of acid halide.

When a carboxylic acid is used in the above-mentioned reaction, an acetylene derivative of general formula (I) wherein s is 1 can be obtained by using the carboxylic acid in an amount of 1–2 equivalents per equivalent of alcohol derivative (III) and carrying out a dehydrating condensation reaction in the presence of a condensing agent.

As said condensing agent, carbodiimides such as N,N'-dicyclohexylcarbodiimide and N-cyclohexyl-N'-(4-diethylamino)-cyclohexylcarbodiimide are preferably used. If necessary, an organic base such as 4-dimethylaminopyridine, 4-pyrrolidinopyridine, pyridine and triethylamine is used in combination therewith.

The condensing agent is used in an amount of 1–1.5 equivalents per equivalent of the carboxylic acid. When said organic base is used in combination with the condensing agent, the organic base is used in an amount of 0.01–0.2 equivalent per equivalent of the condensing agent.

The reaction temperature is usually from −30° C. to 100° C., and preferably from 0° C. to 80° C.

The reaction time is not particularly limited, but the point in time when the starting alcohol (III) has disappeared can be taken as end point of the reaction.

After completion of the reaction, the acetylene derivative (I) wherein s is 1 can be recovered in a high yield by conventional separating means such as extraction, phase separation, concentration or the like. If necessary, the product may be purified by the method of column chromatography, recrystallization or the like.

Next, an acetylene derivative of general formula (I) wherein s is 0 can be produced by reacting an alcohol derivative represented by the above-mentioned general formula (III) with an alkylating agent represented by the following general formula:

$$R^2-Z$$

wherein $R^2$ is as defined above and Z represents halogen atom or —$OSO_2R''$ in which R" represents lower alkyl group or optionally substituted phenyl group.

Herein, the term "alkylating agent" means a halide or a sulfonic ester having a substituent $R^2$. These compounds can be produced from the corresponding alcohol according to known processes.

In the alkylating agent, the substituent R2 may be an optically active group.

This reaction is usually carried out in the presence of a basic substance.

Said alkylating agent is used in an arbitrary amount not smaller than one equivalent per equivalent of alcohol derivative (III). Usually its amount is in the range of from 1 to 5 equivalents.

The above-mentioned reaction is usually carried out in the presence of a solvent. Examples of the solvents usable include single members and mixtures thereof the solvents inert to the reaction such as ethers, ketones, aliphatic and aromatic hydrocarbons, halogenated hydrocarbons, aprotic polar solvents and the like, of which examples include tetrahydrofuran, ethyl ether, acetone, methyl ethyl ketone, toluene, benzene, chlorobenzene, dichloromethane, dichloroethane, chloroform, carbon tetrachloride, hexane, dimethylformamide, dimethyl sulfoxide, hexamethylphosphorylamide, N-methylpyrrolidone and the like. The quantity of these solvents is not particularly limited.

Examples of the basic substance include alkali metal hydrides such as sodium hydride, potassium hydride and the like, alkali metals such as lithium, sodium, potassium and the like, alkali metal alcoholates such as sodium ethylate, sodium methylate and the like, alkali carbonates such as sodium carbonate, potassium carbonate and the like, butyllithium, and the like.

The basic substance must be used in an amount of at least one equivalent per equivalent of alcohol derivative (III), and usually in an amount of 1.1–5 equivalents, though the upper limit of its amount is not critical.

The reaction temperature is usually in the range of from −50° C. to 120° C., and preferably from −30° C. to 100° C.

The reaction time is not particularly limited, but the point in time when the starting alcohol derivative (III) has disappeared may be taken as end point of the reaction.

After completion of the reaction, the objective acetylene derivative represented by general formula (I) wherein s is 0 can be isolated from the reaction mixture according to the conventional separating means such as extraction, phase separation, concentration, etc. If necessary, the product may be purified by column chromatography, recrystallization, etc.

In the alkylation reaction, when the substituent Z of the alkylating agent is an iodine atom, silver oxide may be used in place of said basic substance.

In this case, said silver oxide must be used in an amount of at least one equivalent per equivalent of alcohol derivative (III). Although upper limit of the amount of the silver oxide is not critical, the upper limit is preferably 5 equivalents per equivalent of alcohol derivative (III).

When the alkylation is carried out in the presence of silver oxide, the alkylating agent in which the substituent Z is an iodine atom is used in an arbitrary amount not smaller than one equivalent per equivalent of alcohol derivative (III), and preferably in an amount of 2–10 equivalents per equivalent of the As the reaction solvent, an excessive amount of alkylating agent in which the substituent is iodine atom can be used as a solvent. Apart from it, solvents inert to the reaction such as ethers, ketones, hydrocarbons and the like, of which examples include tetrahydrofuran, ethyl ether, dioxane, acetone, methyl ethyl ketone, benzene, toluene, hexane and the like, may also be used either singly or in the form of mixture.

The reaction temperature is usually in the range of from 0° C. to 150° C., and preferably from 20° C. to 100° C.

The reaction time is usually from one hour to 20 days.

From the reaction mixture, the acetylene derivative of formula (I) wherein s is 0 is taken out by removing silver salt by filtration and thereafter carrying out conventional aftertreatment such as extraction, phase separation, concentration, etc.

If necessary, the product may be purified by column chromatography or the like.

The process for obtaining an acetylene derivative from alcohol derivative (III) is as has been mentioned above. As examples of the substituent $R^2$ of the carboxylic acid and the alkylating agent used therein, the following can be referred to:

methyl, ethyl, propyl, isopropyl, butyl, isobutyl, pentyl, isopentyl, hexyl, heptyl, octyl, nonyl, decyl, undecyl, dodecyl, tridecyl, tetradecyl, pentadecyl, hexadecyl, heptadecyl, propenyl, 2-butenyl, 3-butenyl, 3-hexenyl, 2-butinyl, 3-hexinyl, cyclopropyl, 2,2-dimethylcyclopropyl, cyclopentyl, cyclohexyl, octadecyl, nonadecyl, eicosyl, methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, propoxymethyl, propxyethyl, propoxypropyl, propoxybutyl, propoxypentyl, propoxyhexyl, propoxyheptyl, propoxyoctyl, propoxynonyl, propoxydecyl, butoxymethyl, butoxyethyl, butoxypropyl, butoxybutyl, butoxypentyl, butoxyhexyl, butoxyheptyl, butoxyoctyl, butoxynonyl, butoxydecyl, pentyloxymethyl, pentyloxyethyl, pentyloxypropyl, pentyloxybutyl, pentyloxypentyl, pentyloxyhexyl, pentyloxyheptyl, pentyloxyoctyl, pentyloxynonyl, pentyloxydecyl, hexyloxymethyl, hexyloxyethyl, hexyloxypropyl, hexyloxybutyl, hexyloxypentyl, hexyloxyhexyl, hexyloxyheptyl, hexyloxyoctyl, hexyloxynonyl, hexyloxydecyl, heptyloxymethyl, heptyloxyethyl, heptyloxypropyl, heptyloxybutyl, hexyloxypentyl, octyloxymethyl, octyloxyethyl, octyloxypropyl, decyloxymethyl, decyloxyethyl, decyloxypropyl, 1-methylethyl, 1-methylpropyl, 1-methylbutyl, 1-methylpentyl, 1-methylhexyl, 1-methylheptyl, 1-methyloctyl, 2-methylethyl, 2-methylbutyl, 2,3-dimethylbutyl, 2,3,3-trimethylbutyl, 2-methylpentyl, 3-methylpentyl, 2,3-dimethylpentyl, 2,4-dimethylpentyl, 2,3,3,4-tetramethylpentyl, 2-methylhexyl, 3-methylhexyl, 4-methylhexyl, 2,5-dimethylhexyl, 2-methylheptyl, 2-methyloctyl, 2-trihalomethylpentyl, 2-trihalomethylhexyl, 2-trihalomethylheptyl, 2-haloethyl, 2-halopropyl, 3-halopropyl, 3-halo-2-methylpropyl, 2,3-dihalopropyl, 2-halobutyl, 3-halobutyl, 4-halobutyl, 2,3-dihalobutyl, 2,4-dihalobutyl, 3,4-dihalobutyl, 2-halo-3-methylbutyl, 2-halo-3,3-dimethylbutyl, 2-halopentyl, 3-halopentyl, 4-halopentyl, 5-halopentyl, 2,4-dihalopentyl, 2,5-dihalopentyl, 2-halo-3-methylpentyl, 2-halo-4-methylpentyl, 2-halo-3-monohalomethyl-4-methylpentyl, 2-halohexyl, 3-halohexyl, 4-halohexyl, 5-halohexyl, 6-halohexyl, 2-haloheptyl, 2-halooctyl and the like, provided that the term "halo" used in these examples means fluorine, chlorine or bromine.

Regarding the carboxylic acid, examples of $R^2$ are the same as the above, in addition to which halomethyl, 1-haloethyl, 1-halopropyl, 1-halobutyl, 1-halopentyl, 1-halohexyl, 1-haloheptyl, 1-halooctyl and the like can also be referred to.

These alkyl groups or alkoxyalkyl groups may be of straight chain type, branched chain type or cyclic type. In the cases of branched chain type and cyclic type, the alkyl or alkoxyalkyl group may be optically active.

Among the carboxylic acids having substituent R2 exemplified above, some of the optically active carboxylic acids can be obtained by an oxidation of the corresponding alcohols or a reductive deamination of the corresponding amino acids; and some other optically active carboxylic acids can be obtained from the natural world or derived from the following optically active amino acids and optically active oxy acids obtained by optical resolution.

Among the alkylating agents having a substituent $R^2$, some of the optically active ones can be easily obtained from the corresponding alcohols according to known methods. Among such corresponding alcohols, some ones can be obtained by asymmetric reduction of the corresponding ketones using an asymmetric metallic catalyst or a microorganism or an enzyme; and some others are obtained from the natural world or can be derived from the following optically active amino acids or optically active oxy acids obtained by optical resolution:

alanine, valine, leucine, isoleucine, phenylalanine, threonine, allothreonine, homoserine, alloisoleucine, tert-leucine, 2-aminobutyric acid, norvaline, norleucine, ornithine, lysine, hydroxylysine, phenylglycine, aspartic acid, glutamic acid, mandelic acid, tropic acid, 3-hydroxylbutyric acid, malic acid, tartaric acid, isopropylmalic acid and the like.

The acetylene derivative represented by general formula (I) obtained herein can be converted a compound represented by the general formula (II):

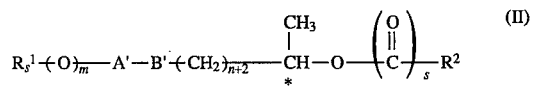

wherein $R_S^1$, $R^2$, m, n and the mark * are as defined above, A' is the same as A, and B' is the same as B, by the method of hydrogenation using hydrogen and a hydrogenating catalyst.

As the hydrogenating catalyst used in the above reaction, metallic catalysts such as Raney nickel and palladium catalysts are preferred. Concrete examples of the metallic catalyst include palladium-carbon, palladium oxide, palladium black, palladium chloride, and the like.

Said hydrogenating catalyst is used in an amount of usually 0.001–0.5 time by weight and preferably 0.005–0.3 time by weight as much as the acetylene derivative represented by general formula (I). The reaction is carried out in a solvent. As the solvent, for example, solvents inert to the reaction such as hydrocarbons, alcohols, ethers, ketones, esters, halogenated hydrocarbons, amides and the like, of which examples include water, dioxane, tetrahydrofuran, methanol, ethanol, n-propyl alcohol, acetone, dimetylformamide, toluene, dichloromethane, ethyl acetate and the like, are used either singly or in the form of mixture.

The reaction is carried out under ordinary or elevated pressure. Preferably, the point in time when absorption of hydrogen has reached 1–1.2 equivalents per equivalent of the starting acetylene derivative represented by general formula (I) is taken as end point of the reaction.

The reaction is carried out at a temperature of from −10° C. to 100° C., preferably at from 10° C. to 60° C.

After completion of the reaction, the objective compound represented by general formula (II) can be isolated from the reaction mixture by removing the catalyst therefrom by filtration or the like and concentrating the filtrate. If necessary, the product may be purified by recrystallization, column chromatography, etc.

The alcohols represented general formula (III) can be synthesized in the following manner.

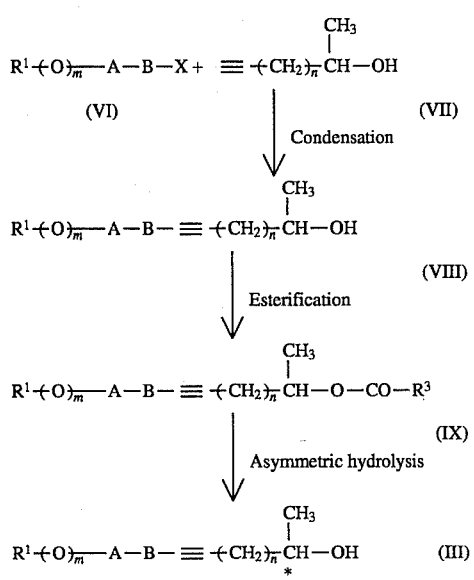

wherein $R^1$, A, B and m are as defined above, X represents halogen atom such as chlorine atom, bromine atom, iodine atom or the like, and $R^3$ represents lower alkyl group.

Now, the condensation reaction in the above-mentioned reaction scheme will be mentioned in more detail.

The compound represented by general formula (VIII) is obtained by reacting a halide represented by general formula (VI) with an acetylene compound represented by general formula (VII) in the presence of a metallic catalyst and a basic substance.

The starting compounds represented by general formulas (VI) and (VII) can be produced according to the methods mentioned in literature.

The acetylene compound (VII) is used in an amount of usually 0.9–10 equivalents and preferably 1–2 equivalents per equivalent of halide (VI).

As the metallic catalyst used in the above reaction, palladium chloride, palladium acetate, triphenylphosphine palladium complex, palladium/carbon and the like can be used in palladium type catalysts, and similar compounds can be used in nickel type and rhodium type catalysts, too.

Said metallic catalyst is used in an amount falling in the range of from 0.001 to 0.1 equivalent per equivalent of starting halide (VI).

This reaction requires to use, in addition to the above-mentioned metallic catalyst, a trivalent phosphorus compound or a trivalent arsenic compound as a co-catalyst, which are compounds represented by general formula (X):

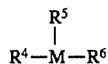

wherein M represents phosphorus atom or arsenic atom, and $R^4$, $R^5$ and $R^6$, identical or different, represent alkyl group, aryl group, alkoxy group, aryloxy group or halogen atom. Concrete examples of said compound include tri-n-butylphosphine, triphenylphosphine, tri-o-tolylphosphine, tri-o-tolyl phosphite, phosphorus trichloride, triphenylarsenic and the like.

These phosphorus compound or arsenic compound is used in an amount of 0.5–50 equivalents and preferably 10–30 equivalents per equivalent of the above-mentioned metallic catalyst.

In addition to these catalysts, a copper catalyst is used. As said copper catalyst, copper iodide, copper bromide, copper oxide, copper cyanide and the like are used. Said copper catalyst is used in an amount falling in the range of from 0,001 to 0.1 equivalent per equivalent of the starting halide (VI). Of course, the copper catalyst may be used in an amount larger than the above, though the use of such a large amount brings about no particular merit.

As said basic substance, alkali metal carbonates, carboxylic acid salts, alkoxides, hydroxides and organic bases can be used, among which tertiary amines and secondary amines (organic bases) are preferred. Examples of said organic amines include triethylamine, di-isopropylethylamine, tri-n-butylamine, tetramethylethylenediamine, dimethylaniline and the like.

The organic base is used in an amount of 1–5 equivalents per equivalent of halide (VI).

If necessary, acetonitrile, tetrahydrofuran, dimethylformamide, hexamethylphosphorylamide, N-methylpyrrolidone, methanol and the like can be used as a reaction solvent. It is also possible to use the above-mentioned basic substance in a large amount as a solvent.

Amount of these reaction solvents is not particularly limited.

This reaction is usually carried out in an inert gas such as nitrogen, argon, and the like.

In this process, yield of the objective compound (VIII) can be improved by elevating the reaction temperature. However, yield of by-products increases at an excessively high temperature. Accordingly, the reaction temperature is usually from 15° C. to 190° C., and preferably from 40° C. to 150° C.

After completion of the reaction, compound (VIII) can be isolated by conventional means such as extraction, distillation, recrystallization, etc.

If a compound represented by general formula

wherein n and $R^3$ are as defined above, is used in place of the compound (VII), the subsequent esterification reaction can be omitted, and an ester derivative (IX) can be obtained.

As examples of the acetylene derivative represented by general formula (I) obtained according to the process mentioned above, the following can be referred to:

2-alkyl-5-(4-(3-substituted-1-butynyl)phenylpyrimidine,
2-alkyloxy-5-(4-(3-substituted-1-butynyl)phenyl)pyrimidine,
5-alkyl-2-(4-(3-substituted-1-butynyl)phenyl)pyrimidine,
5-alkyloxy-2-(4-(3-substituted-1-butynyl)phenyl)pyrimidine,
2-(4-alkylphenyl)-5-(3-substituted-1-butynyl)pyrimidine,
2-(4-alkyloxyphenyl)-5-(3-substituted-1-butynyl)pyrimidine,
5-(4-alkylphenyl)-2-(3-substituted-1-butynyl)pyrimidine,
5-(4-alkyloxyphenyl)-2-(3-substituted-1-butynyl)pyrimidine,
3-(4-alkylphenyl)-6-(3-substituted-1-butynyl)pyridazine,
3-(4-alkyloxyphenyl)-6-(3-substituted-1-butynyl)pyridazine,
3-alkyl-6-(4-(3-substituted-1-butynyl))pyridazine,
3-alkyloxy-6-(4-(3-substituted-1-butynyl))pyridazine,
2-(4-alkylphenyl)-5-(3-substituted-1-butynyl)pyrazine,
2-(4-alkyloxyphenyl)-5-(3-substituted-1-butynyl)pyrazine,
5-(4-alkylphenyl)-5-(3-substituted-1-butynyl)pyrazine,
5-(4-alkyloxyphenyl)-5-(3-substituted-1-butynyl)pyrazine,
4'-alkyl-4-(3-substituted-1-butynyl)biphenyl, 4'-alkyloxy-4-(3-substituted-1-butynyl)biphenyl,
2-alkyl-5-(4-(3-substituted-1-butynyl)phenyl)pyridine,
2-alkyloxy-5-(4-(3-substituted-1-butynyl)phenyl)pyridine,
3-alkyl-6-(4-(3-substituted-1-butynyl)phenyl)pyridine,
3-alkyloxy-5-(4-(3-substituted-1-butynyl)phenyl)pyridine,
2-(4-alkylphenyl)-5-(3-substituted-1-butynyl)pyridine,
2-(4-alkyloxyphenyl)-5-(3-substituted-1-butynyl)pyridine,
3-(4-alkylphenyl)-6-(3-substituted-1-butynyl)pyridine,
3-(4-alkyloxyphenyl)-6-(3-substituted-1-butynyl)pyridine,
2-alkyl-6-(3-substituted-1-butynyl)naphthalene,
2-alkyloxy-6-(3-substituted-1-butynyl)naphthalene,
2-alkyl-6-(3-substituted-1-butynyl)quinoxaline,
2-alkyloxy-6-(3-substituted-1-butynyl)quinoxaline,
2-(3-substituted-1-butynyl)-6-alkylquinoxaline,
2-(3-substituted-1-butynyl)-6-alkyloxyquinoxaline,
2-alkyl-6-(3-substituted-1-butynyl)quinazoline,
2-alkyloxy-6-(3-substituted-1-butynyl)quinazoline,
2-(3-substituted-1-butynyl)-6-alkylquinazoline,
2-(3-substituted-1-butynyl)-6-alkyloxyquinazoline,
and the compounds in which the (3-substituted-1-butynyl) group of the above-mentioned compounds is replaced by one of (4-substituted-1-pentynyl) group, (5-substituted-1-hexynyl) group, (6-substituted-1-heptynyl) group, (7-substituted-1-octynyl) group, (8-substituted-1-nonynyl) group and (9-substituted-1-decynyl) group.

In the compound names shown above, the term "alkyl" means a saturated or unsaturated alkyl having 3–20 carbon atoms; the term "alkyloxy" means a saturated or unsaturated alkyloxy having 3–20 carbon atoms; the term "substituted" means alkyl($R^2$)oxy group or alkyl($R^2$)carbonyloxy group; and the term "alkyl($R^2$)" means a $C_{1-20}$ saturated or unsaturated alkyl optionally substituted by halogen atom or $C_{2-20}$ alkoxyalkyl group of which examples have been mentioned above.

The compounds represented by general formula (II) obtainable by reducing an acetylene derivative of this invention represented by general formula (I) can be synthesized also via another route, namely by reducing an alcohol derivative represented by general formula (III) and then reacting it with $R^2Z$ or $R^2COR'$ as shown below:

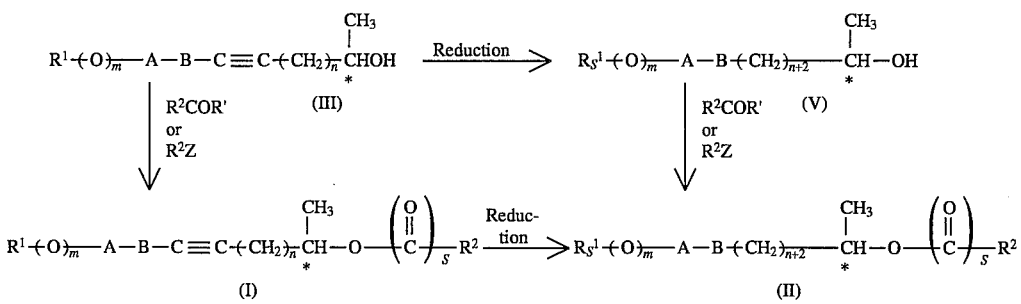

wherein $R^1$, $R_S^1$, $R^2$, A, B, m, n, s and the mark * are as defined above.

In the reaction mentioned above, the reduction from alcohol derivative (III) to saturated alcohol derivative (V) can be practiced by a hydrogenation using hydrogen and a hydrogenating catalyst. As for the concrete conditions and catalyst, the same conditions and catalyst as in the reaction for reducing acetylene derivative (I) into compound (II) can be adopted as they are.

The reaction from a saturated alcohol derivative into compound (II) can be practiced by using $R^2COR'$ or $R^2Z$. In this case, too, the same concrete conditions and reagent as in the reaction for obtaining acetylene derivative from alcohol derivative (III) can be adopted as they are.

As concrete examples of the compound (II) thus obtained, the compounds in which the (3-substituted-1-butynyl) group in the above-mentioned examples of acetylene derivative (I) is replaced by one of the following groups can be referred to: (3-substituted-butyl), (4-substituted-pentyl), (5-substituted-hexyl), (6-substituted-heptyl), (7-substituted-octyl), (8-substituted-nonyl) and (9-substituted-decyl).

The acetylene alcohol derivative represented by general formula (I'):

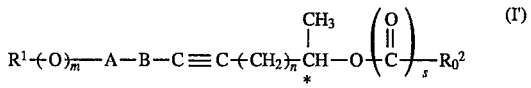

wherein $R_o^2$ represents $C_{1-20}$ saturated or unsaturated alkyl group optionally substituted by halogen atom or $C_{2-20}$ alkoxyalkyl group, and $R^1$, m, n and the mark * are as defined above, provided that when s is 0, $R_o^2$ may be a hydrogen atom, can be produced according to the process mentioned below.

Thus, the acetylene alcohol derivative represented by general formula (I') is obtained by reacting a halide represented by general formula (VI):

wherein $R^1$, A, B and m are as defined above and X is halogen atom, with an acetylene compound represented by general formula (VII*):

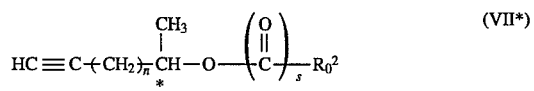

wherein $R_o^2$, n, s and the mark * are as defined above, and a palladium catalyst in the presence of a basic substance.

Next, the process for producing the acetylene derivative represented by general formula (I') is mentioned below.

Fundamentally, this reaction is similar to the case of the alcohol represented by general formula (III).

The starting materials are a halide represented by general formula (VI) and an acetylene compound represented by general formula (VII*).

Acetylene compound (VII*) is obtained by, for example, an enzymatic resolution of racemic alcohol, as mentioned below. More concretely saying, esters represented by general formula (VII*) wherein s is 1 are synthesized by acylation, while ethers represented by general formula (VII*) wherein s is 0 are synthesized by alkylation.

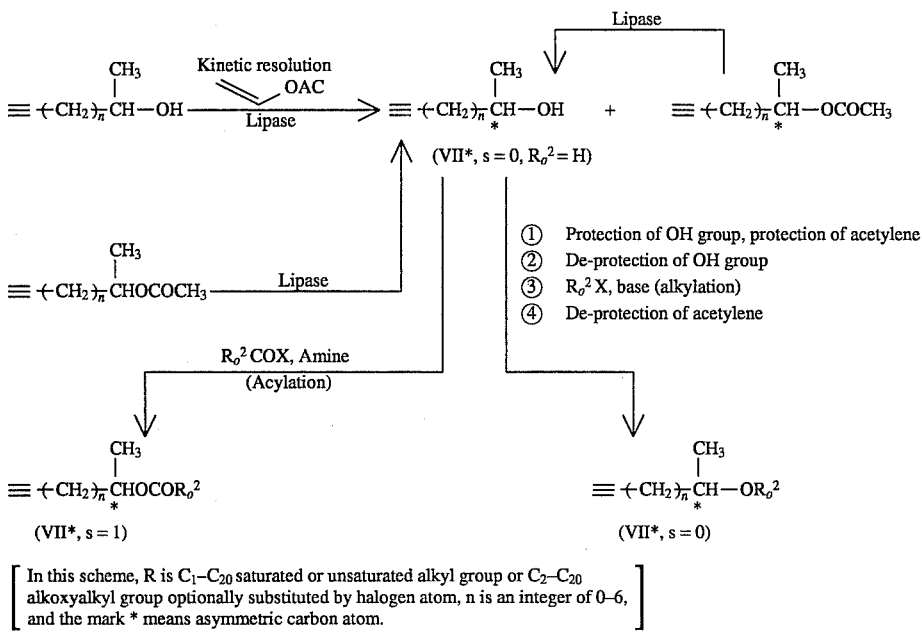

[In this scheme, R is $C_1$–$C_{20}$ saturated or unsaturated alkyl group or $C_2$–$C_{20}$ alkoxyalkyl group optionally substituted by halogen atom, n is an integer of 0–6, and the mark * means asymmetric carbon atom.]

In the reaction for obtaining acetylene alcohol derivative (I') from halide (VI) and acetylene compound (VII*), the acetylene compound (VII*) is used in an amount of usually 0.9–10 equivalents and preferably 1–2 equivalents, per equivalent of the halide (VI).

As the metallic catalyst, palladium chloride, palladium acetate, triphenylphosphine palladium complex, palladium/carbon and the like are used in the palladium type catalysts. Regarding nickel type and rhodium catalyst, similar catalysts to the above-mentioned ones are used.

These metallic catalysts are used in an amount falling in the range of from 0.001 to 0.1 equivalent per equivalent of the starting halide (VI). In this reaction, a trivalent phosphorus compound or a trivalent arsenic compound must be used as a co-catalyst in addition to the above-mentioned metallic catalyst. The co-catalyst is a compound represented by general formula (X):

$$\begin{array}{c} R^5 \\ | \\ R^4-Y-R^6 \end{array} \quad (X)$$

wherein Y represents phosphorus atom or arsenic atom and $R^4$, $R^5$ and $R^6$, identical or different, represent alkyl group, aryl group, alkoxy group, aryloxy group or halogen atom. Concrete examples thereof include tri-n-butylphosphine, triphenylphosphine, tri-o-tolyphosphine, tri-o-tolyl phosphite, phosphorus trichloride, triphenylarsene, and the like.

The phosphorus compound or arsenic compound is used in an amount of 0.5–50 equivalents and preferably 10–30 equivalents per equivalent of the above-mentioned metallic catalyst.

Further, a copper catalyst is used in addition to these catalysts. As said copper catalyst, copper iodide, copper bromide, copper chloride, copper oxide, copper cyanide and the like can be referred to. The copper catalyst is used in an amount of 0.001–0.1 equivalent per equivalent of the starting halide (VI). Of course, the copper catalyst may be used in an amount larger than the above, though the use of such a large amount brings about no particular merit.

As the basic substance, carbonates, carboxylates, alkoxides, hydroxides and the like of alkali metals, as well as organic bases, can be referred to. Among these substances, tertiary amines and secondary amines (organic bases) are preferred, of which examples include diethylamine, triethylamine, diisopropylethylamine, tri-n-butylamine, tetramethylethylenediamine, dimethylaniline and the like.

The base is used usually in an amount of 1–5 equivalents per equivalent of the halide (VI).

If necessary, an appropriate solvent such as acetonitrile, tetrahydrofuran, dimethylformamide, hexamethylphosphorylamide, N-methylpyrrolidone, methanol and the like may be used as a reaction solvent.

Further, the above-mentioned bases may also be used as a solvent.

The amount of these reaction solvents is not particularly limited.

The reaction is usually carried out in an inert gas such as nitrogen, argon or the like.

In the reaction, the yield of the objective compound can be improved by enhancing reaction temperature. However, the yield of by-products increases at an excessively elevated temperature. Accordingly, the reaction temperature is usually 15° C. to 160° C., and preferably 30° C. to 140° C.

After completion of the reaction, optically active acetylene alcohol derivative (I') can be obtained by a conventional means such as extraction, distillation, recrystallization and the like. If necessary, the product can be purified by column chromatography, recrystallization or the like.

Next, examples of the compound represented by general formula (I') obtained according to this invention are shown below:

5-alkyl-2-(3-hydroxy-1-butynyl)phenylpyrimidine,
5-alkyloxy-2-(3-hydroxy-1-butynyl)phenylpyrimidine,
2-alkylphenyl-5-(3-hydroxy-1-butynyl)pyrimidine,
2-alkyloxyphenyl-5-(3-hydroxy-1-butynyl)pyrimidine,
2-alkyl-5-(3-hydroxy-1-butynyl)phenylpyrimidine,
2-alkyloxy-5-(3-hydroxy-1-butynyl)phenylpyrimidine,
5-alkylphenyl-2-(3-hydroxy-1-butynyl)pyrimidine,
5-alkyloxyphenyl-2-(3-hydroxy-1-butynyl)pyrimidine,
4'-alkyl-4-(3-hydroxy-1-butynyl)biphenyl,
4'-alkyloxy-4-(3-hydroxy-1-butynyl)biphenyl,
2-(4-alkylphenyl)-5-(3-hydroxy-1-butynyl)pyridine,
2-(4-alkyloxyphenyl)-5-(3-hydroxy-1-butynyl)pyridine,
5-(4-alkylphenyl)-2-(3-hydroxy-1-butynyl)pyridine, 5-(4-alkyloxyphenyl)-2-(3-hydroxy-1-butynyl)pyridine,
2-alkyl-6-(3-hydroxy-1-butynyl)naphthalene,
2-alkyloxy-6-(3-hydroxy-1-butynyl)naphthalene,
3-alkyl-6-(3-hydroxy-1-butynyl)phenylpyridazine,
3-alkyloxy-6-(3-hydroxy-1-butynyl)phenylpyridazine,
3-(4-alkylphenyl)-6-(3-hydroxy-1-butynyl)pyridazine,
3-(4-alkyloxyphenyl)-6-(3-hydroxy-1-butynyl)pyridazine,
2-alkyl-5-(3-hydroxy-1-butynyl)phenylpyrazine,
2-alkyloxy-5-(3-hydroxy-1-butynyl)phenylpyrazine,
2-(4-alkylphenyl)-5-(3-hydroxy-1-butynyl)pyrazine,
2-(4-alkyloxyphenyl)-5-(3-hydroxy-1-butynyl)pyrazine,
2-alkyl-6-(3-hydroxy-1-butynyl)quinazoline,
2-alkyloxy-6-(3-hydroxy-1-butynyl)quinazoline,
6-alkyl-2-(3-hydroxy-1-butynyl)quinazoline,
6-alkyloxy-2-(3-hydroxy-1-butynyl)quinazoline,
2-alkyl-6-(3-hydroxy-1-butynyl)quinoxaline,
2-alkyloxy-6-(3-hydroxy-1-butynyl)quinoxaline,
6-alkyl-2-(3-hydroxy-1-butynyl)quinoxaline,
6-alkyloxy-2-(3-hydroxy-1-butynyl)quinoxaline,
and the compounds in which the substituent (3-hydroxy-1-butynyl) has been replaced by one of 4-hydroxy-1-pentynyl, 5-hydroxy-1-hexynyl, 6-hydroxy-1-heptynyl and 7-hydroxy-1-octynyl groups.

In the compound names presented above, the term "alkyl" means saturated or unsaturated alkyl group having 3–20 carbon atoms.

Examples of the compound represented by formula (I') further include the following:
5-alkyl-2-(3-substituted-1-butynyl)phenylpyrimidine,
5-alkyloxy-2-(3-substituted-1-butynyl)phenylpyrimidine,
2-alkylphenyl-5-(3-substituted-1-butynyl)pyrimidine,
2-alkyloxyphenyl-5-(3-substituted-1-butynyl)pyrimidine,
2-alkyl-5-(3-substituted-1-butynyl)phenylpyrimidine,
2-alkyloxy-5-(3-substituted-1-butynyl)phenylpyrimidine,
5-alkylphenyl-2-(3-substituted-1-butynyl)pyrimidine,
5-alkyloxyphenyl-2-(3-substituted-1-butynyl)pyrimidine,
4'-alkyl-4-(3-substituted-1-butynyl)biphenyl,
4'-alkyloxy-4-(3-substituted-1-butynyl)biphenyl,
2-(4-alkylphenyl)-5-(3-substituted-1-butynyl)pyridine,
2-(4-alkyloxyphenyl)-5-(3-substituted-1-butynyl)pyridine,
5-(4-alkylphenyl)-2-(3-substituted-1-butynyl)pyridine,
5-(4-alkyloxyphenyl)-2-(3-substituted-1-butynyl)pyridine,
2-alkyl-6-(3-substituted-1-butynyl)naphthalene,
2-alkyloxy-6-(3-substituted-1-butynyl)naphthalene,
3-alkyl-6-(3-substituted-1-butynyl)phenylpyridazine,
3-alkyloxy-6-(3-substituted-1-butynyl)phenylpyridazine,
3-(4-alkylphenyl)-6-(3-substituted-1-butynyl)pyridazine,
3-(4-alkyloxyphenyl)-6-(3-substituted-1-butynyl)pyridazine,
2-alkyl-5-(3-substituted-1-butynyl)phenylpyrazine,
2-alkyloxy-5-(3-substituted-1-butynyl)phenylpyrazine,
2-(4-alkylphenyl)-5-(3-substituted-1-butynyl)pyrazine,
2-(4-alkyloxyphenyl)-5-(3-substituted-1-butynyl)pyrazine,
2-alkyl-6-(3-substituted-1-butynyl)quinazoline,
2-alkyloxy-6-(3-substituted-1-butynyl)quinazoline,
6-alkyl-2-(3-substituted-1-butynyl)quinazoline,
6-alkyloxy-2-(3-substituted-1-butynyl)quinazoline,
2-alkyl-6-(3-substituted-1-butynyl)quinoxaline,
2-alkyloxy-6-(3-substituted-1-butynyl)quinoxaline,
6-alkyl-2-(3-substituted-1-butynyl)quinoxaline,
6-alkyloxy-2-(3-substituted-1-butynyl)quinoxaline,
and the compounds in which the substituent (3-substituted-1-butynyl) has been replaced by one of 4-substituted-1-pentynyl, 5-substituted-1-hexynyl, 6-substituted-1-heptynyl and 7-substituted-1-octynyl groups.

In the compound names presented above, the term "alkyl" means saturated or unsaturated alkyl groups having 3–20 carbon atoms, and the term "substituted" means $C_{1-20}$ saturated or unsaturated alkyl or alkylcarbonyl group optionally substituted by halogen atom, or $C_{2-20}$ alkoxyalkyl or alkoxyalkylcarbonyl group.

Next, the process for reducing the optically active acetylene alcohol derivative (I') herein obtained to produce an optically active saturated alcohol represented by general formula (II'):

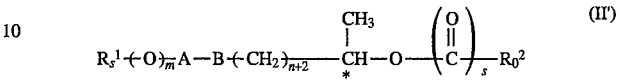

$$R_s^1{+}O{)_m}A-B{+}CH_2{)_{n+2}}\overset{CH_3}{\underset{*}{CH}}-O-\left(\overset{O}{\overset{\|}{C}}\right)_s R_o^2 \quad (II')$$

wherein $R_s^1$, $R_o^2$, A, B, m, n, s and the mark * are as defined above, will be mentioned.

The reduction can be carried out by hydrogenating an optically active acetylene alcohol derivative (I') with hydrogen and hydrogenating catalyst.

As the hydrogenating catalyst of the reaction, Raney nickel and palladium type metallic catalysts are preferably used, of which concrete examples include palladium-carbon, palladium oxide, palladium black, palladium chloride and the like.

Said hydrogenating catalyst is used in an amount of usually 0.001–0.5 time by weight and preferably 0.005–0.3 time by weight based on the optically active acetylene alcohol derivative (I'). The reaction is usually carried out in a solvent. As the solvent, the solvents inert to the reaction such as hydrocarbons, alcohols, ethers, ketones, esters, halogenated hydrocarbons, amides and the like of which examples include water, dioxane, tetrahydrofuran, methanol, ethanol, n-propyl alcohol, acetone, dimethylformamide, toluene, dichloromethane, ethyl acetate and the like, are used either singly or in the form of mixture.

The reaction is carried out under an ordinary or elevated pressure of hydrogen. Preferably, the point in time when absorption of hydrogen has reached 2–2.2 equivalents per equivalent of the starting optically active acetylene alcohol derivative (I') is taken as end point of the reaction.

The reaction is carried out at −10° C. to 100° C., and preferably at 10° C. to 60° C.

After completion of the reaction, the objective optically active saturated alcohol (II') can be taken out from the reaction mixture by removing the catalyst by filtration or the like, followed by concentration or the like. If necessary, the product may be purified by recrystallization, column chromatography or the like.

The optically active alcohol derivative (III) can be produced by asymmetrically hydrolyzing an ester derivative represented by general formula (IX):

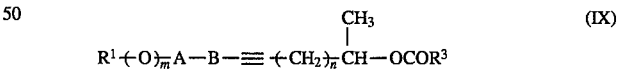

$$R^1{+}O{)_m}A-B-{\equiv}{+}CH_2{)_n}\overset{CH_3}{\underset{|}{CH}}-OCOR^3 \quad (IX)$$

wherein $R^3$ represents a lower alkyl group and $R^1$, m, n, A and B are as defined above, with an esterase having an ability to preferentially hydrolyze any one of the optically active isomers of the ester derivative.

As used in the invention, the term "esterase" means "esterase in the broad sense", which involves lipase, too.

The microorganism producing esterase, used in this invention, may be any of the microorganisms producing an esterase having an ability to asymmetrically hydrolyze esters; and it is not particularly limited.

Concrete examples of said microorganism include the microorganisms belonging to, for example, Genus Enterobacter, Genus Arthrobacter, Genus Brevibacterium, Genus Pseudomonas, Genus Alcaligenes, Genus Micrococcus, Genus Chromobacterium, Genus Microbacterium, Genus Corynebacterium, Genus Bacillus, Genus Lactobacillus, Genus Trichoderma, Genus Candida, Genus Saccharomyces, Genus Rhodotolura, Genus Cryptococcus, Genus Torulopsis, Genus Pichia, Genus Penicillium, Genus Aspergillus, Genus Rhizopus, Genus Mucor, Genus Aureobasidium, Genus Actinomucor, Genus Nocardia, Genus Streptomyces, Genus Hansenula and Genus Achromobactor.

Culture of the above-mentioned microorganism is usually carried out in the conventional manner by the method of liquid culture, to obtain a culture fluid.

For example, a sterilized liquid medium [for molds and yeasts, malt extract-yeast extract medium (5 g of peptone, 10 g of glucose, 3 g of malt extract and 3 g of yeast extract are dissolved in 1 liter of water and pH is adjusted to 6.5) is used; and for bacteria, sugar-boullion medium (10 g of glucose, 5 g of peptone, 5 g of meat extract and 3 g of NaCl are dissolved in 1 liter of water and pH is adjusted to 7.2) is used] is inoculated with a microorganism and subjected to reciprocal shaking culture usually at 20°–40° C. for 1–3 days. If desired, solid culture may also be carried out.

Some of these esterases originated from microorganisms are marketed and readily available commercially. As concrete examples of commercial esterase, the following can be referred to, for example:

lipase of Genus Pseudomonas [Lipase P (manufactured by Amano Seiyaku)], lipase of Genus Aspergillus [Lipase AP (manufactured by Amano Seiyaku)], lipase of Genus Mucor [Lipase M-AP (manufactured by Amano Seiyaku)], lipase of Candida cylindrasse [Lipase MY (manufactured by Meito Sangyo)], lipase of Genus Alcaligenes [Lipase PL (manufactured by Meito Sangyo)], lipase of Genus Achromobacter [Lipase AL (manufactured by Meito Sangyo)], lipase of Genus Arthrobacter [Lipase Godo BSL (manufactured by Godo Shusei)], lipase of Genus Chromobacterium (manufactured by Toyo Jozo), lipase of Rhizopus delema [Talipase (manufactured by Tanabe Seiyaku)], and lipase of Genus Rhizopus [Lipase Saiken (manufactured by Osaka Saikin Kenkyusho)].

Animal and vegetable esterases are also usable, of which concrete examples include the following:

steapsin, pancreatin, pig liver esterase, and wheat germ esterase.

As the esterase used in this reaction, the enzymes obtained from animals, plants and microorganisms can be used. As for the form in use of the esterase, various forms such as purified enzyme, crude enzyme, enzyme-containing material, culture broth of microorganism, culture product, bacterial cell, filtrate of culture broth, and treated products thereof can be adopted in accordance with need. Combinations of an enzyme and a microorganism are also usable. Further, immobilized enzyme and immobilized bacterial cell prepared by immobilizing them on a resin or the like are also usable.

The asynmmetric hydrolysis is carried out by vigorously stirring a mixture of a starting ester derivative (IX) and the enzyme of a microorganism usually in a buffer solution.

As the buffer solution, conventional inorganic acid salt type buffers such as sodium phosphate buffer, potassium phosphate buffer and the like, and organic acid salt buffers such as sodium acetate buffer, sodium citrate buffer and the like are used. As pH value of the buffer solution, pH 8–11 is preferable in the culture fluids of alkaliphilic fungi or alkali esterases, and and pH 5–8 is preferable in the culture fluids of non-alkaliphilic microorganisms or esterases having no alkali resistance. Concentration is usually 0.05–2M and preferably 0.05–0.5M.

The reaction temperature is usually 10° C. to 60° C. The reaction time is generally 10–70 hours, though these conditions are not limitative.

When a lipase belonging to Genus Pseudomonas or Genus Arthrobacter is used in the asymmetric hydrolysis reaction, an optically active alcohol derivative (III) can be obtained in a relatively high optical purity.

In the asymmetric hydrolysis, an organic solvent inert to the reaction such as toluene, chloroform, methyl isobutyl ketone, dichloromethane and the like may be used in addition to the buffer solution. By the use of said organic solvent, the asymmetric hydrolysis can be carried out advantageously.

By such asymmetric hydrolysis, either one of the optically active isomers of the starting ester derivative (IX) is preferentially hydrolyzed to form an optically active alcohol derivative represented by general formula (III). On the other hand, the other optical isomer of the starting ester derivative (IX) remains as it is as a residue of hydrolysis.

After completion of the hydrolysis, the reaction mixture of hydrolysis is extracted with a solvent such as methyl isobutyl ketone, ethyl acetate, ethyl ether or the like, the solvent is distilled off from the organic layer, and the residue is treated by, for example, column chromatography, whereby the hydrolyzate, namely optically active alcohol derivative (III), can be separated from the residue of hydrolysis, namely optically active ester derivative [namely, the optically active isomer which has not been hydrolyzed among the optically active isomers of the starting ester derivative (IX)].

If necessary, the optically active ester derivative obtained herein may be additionally hydrolyzed to obtain an optically active alcohol derivative (III) which is antipodal to the optically active alcohol obtained above.

The starting compound, namely the ester derivative (IX), can be produced by reacting an ester derivative represented by general formula (VIII):

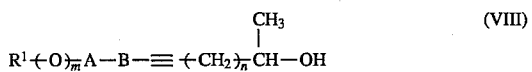

(VIII)

wherein $R^1$, A, B, m and n are as defined above, with a carboxylic acid represented by general formula (XIII):

$R^3COOH$ (XIII)

wherein $R^3$ is as defined above, or a derivative thereof.

In this acylation reaction, the lower alkylcarboxylic acid (XIII) or its derivative functions as an acylating agent. As said acylating agent, acid anhydride or acid halide of lower alkylcarboxylic acid is usually used. As examples of said acid anhydride and acid halide, acetic anhydride, propionic acid anhydride, acetic acid chloride or bromide, propionic acid chloride or bromide, butyryl chloride or bromide, valeryl chloride or bromide, and the like can be referred to.

The reaction between the alcohol derivative (VIII) and lower alkylcarboxylic acid is usually carried out by applying the conditions of esterification, in the presence or absence of a solvent, by the use of a catalyst.

When a solvent is used in this reaction, the solvent includes single members and mixtures thereof of the solvents inert to the reaction such as aliphatic and aromatic hydrocarbons, ethers, ketones, halogenated hydrocarbons, aprotic polar solvents and the like of which examples include tetrahydrofuran, ethyl ether, acetone, methyl ethyl ketone, toluene, benzene, chlorobenzene, dichloromethane, dichlorethane, chloroform, carbon tetrachloride, dimethylformamide, hexane and the like. The amount of the solvent is not limited particularly.

The lower alkylcarboxylic acid used in the above-mentioned reaction must be used in an amount of one equivalent or more per equivalent of the starting alcohol derivative (VIII). Upper limit of its amount is preferably 4 equivalents, though it is not particularly limited.

As the catalyst used in the reaction, organic and inorganic basic substances such as dimethylaminopyridine, triethylamine, tri-n-butylamine, pyridine, picoline, imidazole, sodium carbonate, sodium methylate, potassium hydrogen carbonate and the like can be referred to. Although the amount of the catalyst is not particularly limited, it is usually 1–5 equivalents per equivalent of the alcohol derivative (VIII).

When an organic amine is used as the solvent, the amine can function also as a catalyst, in some cases.

Acids such as toluenesulfonic acid, methanesulfonic acid, sulfuric acid and the like can also be used as a catalyst.

The amount of the catalyst varies with the combination of the lower alkylcarboxylic acid used and the catalyst used, and it cannot be specified always. When an acid halide is used as the lower alkylcarboxylic acid, the catalyst is used in an amount of one equivalent or more per equivalent of the acid halide.

The reaction temperature is usually from −30° C. to 100° C., and preferably from −20° C. to 90° C.

The reaction time is not particularly limited, and the point in time when the starting alcohol derivative (VIII) has disappeared may be taken as end point of the reaction.

After completion of the reaction, the ester derivative (IX) can be obtained in a high yield by conventional separating means such as extraction, phase separation, concentration, recrystallization, etc. If necessary, the product may be purified by column chromatography or the like, although it is also possible to feed the reaction mixture as it is to the subsequent step.

Said ester derivative (IX) can be obtained also by reacting a halide represented by general formula (VI):

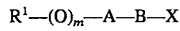

$$R^1—(O)_m—A—B—X \qquad (VI)$$

wherein X represents halogen atom such as chlorine atom, bromine atom, iodine atom or the like and $R^1$, A, B and m are as defined above, with an acetylene compound represented by general formula (XI):

$$CH \equiv C—(CH_2)_n—\underset{\underset{CH_3}{|}}{CH}OCOR^3 \qquad (XI)$$

wherein n and $R^3$ are as defined above, in the presence of a palladium catalyst and a basic substance.

Said alcohol derivative (VIII) can be obtained by reacting halide (VI) with an acetylene compound represented by general formula (VII):

$$CH \equiv C—(CH_2)_n—\underset{\underset{CH_3}{|}}{CH}OH \qquad (VII)$$

wherein n is as defined above.

As the palladium catalyst, basic substance and other catalysts used in this reaction, the same ones as the above-mentioned ones can be used. The reaction solvent and the temperature and other conditions of the reaction may be the same as the above.

From the reaction mixture thus obtained, said alcohol derivative (VIII) can be obtained in a high yield by phase separation, concentration, distillation, recrystallization or the like. In order to produce the ester derivative (IX) in the subsequent step, it is not always necessary to separate the alcohol derivative (VIII), but the reaction mixture may be fed into the subsequent step as it is.

Examples of the compound represented by general formula (III) obtained according to the above-mentioned steps are shown below:

5-alkyl-2-(3-hydroxy-1-butynyl)phenylpyrimidine,
5-alkyloxy-2-(3-hydroxy-1-butynyl)phenylpyrimidine,
2-alkylphenyl-5-(3-hydroxy-1-butynyl)pyrimidine,
2-alkyloxyphenyl-5-(3-hydroxy-1-butynyl)pyrimidine,
2-alkyl-5-(3-hydroxy-1-butynyl)phenylpyrimidine,
2-alkyloxy-5-(3-hydrox-1-butynyl)phenylpyrimidine,
5-alkylphenyl-2-(3-hydroxy-1-butynyl)pyrimidine,
5-alkyloxyphenyl-2-(3-hydroxy-1-butynyl)pyrimidine,
4'-alkyl-4-(3-hydroxy-1-butynyl)biphenyl,
4'-alkyloxy-4-(3-hydroxy-1-butynyl)biphenyl,
2-(4-alkylphenyl)-5-(3-hydroxy-1-butynyl)pyridine,
2-(4-alkyloxyphenyl)-5-(3-hydroxy-1-butynyl)pyridine,
5-(4-alkylphenyl)-2-(3-hydroxy-1-butynyl)pyridine,
5-(4-alkyloxyphenyl)-2-(3-hydroxy-1-butynyl)pyridine,
2-alkyl-6-(3-hydroxy-1-butynyl)naphthalene,
2-alkyloxy-6-(3-hydroxy-1-butynyl)naphthalene,
3-alkyl-6-(3-hydroxy-1-butynyl)phenylpyridazine,
3-alkyloxy-6-(3-hydroxy-1-butynyl)phenylpyridazine,
3-(4-alkylphenyl)-6-(3-hydroxy-1-butynyl)pyridazine,
3-(4-alkyloxyphenyl)-6-(3-hydroxy-1-butynyl)pyridazine,
2-alkyl-5-(3-hydroxy-1-butynyl)phenylpyrazine,
2-alkyloxy-5-(3-hydroxy-1-butynyl)phenylpyrazine,
2-(4-alkylphenyl)-5-(3-hydroxy-1-butynyl)pyrazine,
2-(4-alkyloxyphenyl)-5-(3-hydroxy-1-butynyl)pyrazine,
2-alkyl-6-(3-hydroxy-1-butynyl)quinazoline,
2-alkyloxy-6-(3-hydroxy-1-butynyl)quinazoline,
6-alkyl-2-(3-hydroxy-1-butynyl)quinazoline,
6-alkyloxy-2-(3-hydroxy-1-butynyl)quinazoline,
2-alkyl-6-(3-hydroxy-1-butynyl)quinoxaline,
2-alkyloxy-6-(3-hydroxy-1-butynyl)quinoxaline,
6-alkyl-2-(3-hydroxy-1-butynyl)quinoxaline,
6-alkyloxy-2-(3-hydroxy-1-butynyl)quinoxaline, and the compounds in which the substituent (3-hydroxy-1-butynyl) group is replaced by any one of 4-hydroxy-1-pentynyl, 5-hydroxy-1-hexynyl, 6-hydroxy-1-heptynyl and 7-hydroxy-1-octynyl groups.

Herein, the term "alkyl" in the compound names means saturated or unsaturated alkyl group having 3–20 carbon atoms.

Next, the process for producing an optically active alcohol derivative (V) by reduction of the optically active alcohol derivative (III) obtained herein will be mentioned below.

The reduction can be carried out by hydrogenating the optically active alcohol derivative (III) with hydrogen and a hydrogenating catalyst.

As the hydrogenating catalyst used in the above-mentioned reaction, metallic catalyst such as Raney nickel and palladium type catalysts are preferred, of which concrete examples include palladium-carbon, palladium oxide, palladium black, palladium chloride and the like.

The hydrogenating catalyst is used in an amount of usually 0.001–0.5 time by weight and preferably 0.005–0.3 time by weight based on the optically active alcohol derivative (III). The reaction is carried out in a solvent. As the solvent, the solvents inert to the reaction such as hydrocarbons, alcohols, ethers, ketones, esters, halogenated hydrocarbons and amides of which examples include water, dioxane, tetrahydrofuran, methanol, ethanol, n-propyl alcohol, acetone, dimethylformamide, toluene, dichloromethane, ethyl acetate and the like are used either singly or in the form of a mixture.

The reaction is carried out under an ordinary or elevated pressure of hydrogen. The point in time when absorption of hydrogen has reached 1–1.2 equivalents per equivalent of the starting optically active alcohol derivative (III) is preferably taken as end point of the reaction.

The reaction is carried out at from −10° C. to 100° C., and preferably at from 10° C. to 60° C.

After completion of the reaction, the objective optically active saturated alcohol derivative can be isolated from the reaction mixture by removing the catalyst by filtration or the like and thereafter concentrating the filtrate, etc. If necessary, the product may be purified by recrystallization, column chromatography or the like.

According to an alternative process, the above-mentioned optically active saturated alcohol derivative (V) can be obtained also by hydrogenating an ester derivative represented by general formula (IX) with hydrogen and a hydrogenating catalyst to obtain an ester represented by general formula (XII):

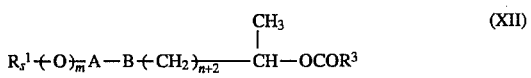

(XII)

wherein $R_s^1$, $R^3$, m, n, A and B are as defined above, and thereafter asymmetrically hydrolyzing the ester with an esterase having an ability to preferentially hydrolyze any one of the optically active isomers of the ester.

This reaction can be practiced by the same procedure as in the above-mentioned process for producing an optically active alcohol derivative (III) from an ester derivative (IX).

The hydrogenating reaction from said ester derivative to said ester can be effected by carrying out a hydrogenation with the same reaction catalysts and under the same reaction conditions as in the above-mentioned reaction for obtaining an optically active saturated alcohol (V) from an optically active alcohol derivative (III).

Further, the above-mentioned ester (XII) can also be produced according to an alternative process, namely by hydrogenating racemic alcohol derivative (VIII) with hydrogen and a hydrogenating catalyst to form a racemic saturated alcohol represented by general formula (XIV):

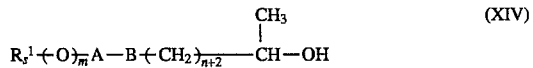

(XIV)

wherein $R_s^1$, A, B, m and n are as defined above, and thereafter reacting it with a carboxylic acid represented by general formula (XIII) or a derivative thereof.

Said hydrogenation reaction and the reaction with carboxylic acid or derivative thereof are both practiced under the reaction conditions described above.

By the reactions mentioned above, a racemic or optically active saturated alcohol of very high purity can be obtained from the novel racemic or optically active alcohol derivative of this invention and, if necessary, via a racemic ester derivative and further via an ester, it can be converted to an optically active saturated alcohol by asymmetric hydrolysis.

The liquid crystal composition of this invention is a composition containing at least one kind of the acetylene derivative represented by general formula (I) as its ingredient. Therein, the compound represented by general formula (I) is used in a proportion ranging from 0.1 to 99.9% by weight and preferably from 1 to 99% by weight, based on the liquid crystal composition obtained therefrom. By using the liquid crystal composition, a liquid crystal element such as photo switching element can be obtained effectively. As for the method for using the liquid crystal composition in these elements, the hitherto known methods can be applied directly without any particular limitation.

Even when the acetylene derivative represented by general formula (I) shows no liquid crystal phase in itself alone, it can be made into a liquid crystal composition which can be used without enhancement in viscosity.

From the viewpoint of chemical stability, the acetylene derivatives represented by general formula (I) are stabler than olefin type of ones. From the viewpoint of liquid crystal property, n is preferably 1 or greater.

Further, when s is equal to 1, the liquid crystal composition is excellent in the action of enhancing spontaneous polarization, and is able to enhance the response speed.

The above-presented description of acetylene derivative (I) in the liquid crystal composition just similarly holds also to the compound represented by general formula (II) obtained by reduction thereof, and the same effect as above can be achieved therefrom as a liquid crystal composition.

Since the acetylene derivative represented by general formula (I) and the compound represented by general formula (II), according to this invention, have quite excellent characteristic properties as liquid crystal compounds, they can be utilized effectively as liquid crystal composition and as liquid crystal element using the same.

WORKING EXAMPLES

Next, this invention is explained in more detail with reference to examples. This invention is by no means limited by these examples.

The temperature of phase series is expressed in the term of °C.

EXAMPLE 1

A four-necked flask equipped with a stirring device and a thermometer was charged with 20 g (51.1 mmol) of 2-(4-bromophenyl)-5-decyloxypyrimidine, 6.5 g (76 mmol) of 4-pentyn-2-ol, 0.34 g (1.78 mmol) of copper iodide, 0.67 g (2.55 mmol) of triphenylphosphine, 0.34 g of bis(triphenylphosphine)-palladium (II) chloride and 200 ml of triethylamine. The content of the flask was heated and stirred in an atmosphere of nitrogen at 90° C. for 8 hours.

After completion of the reaction, the reaction mixture was poured into 200 ml of water, neutralized with dilute sulfuric acid and extracted with toluene-ethyl acetate mixture. The organic solvent layer was washed with water and concentrated under reduced pressure to obtain a yellow-brown colored residue.

The residue was purified by silica gel column chromatography using toluene-ethyl acetate mixture as eluent to obtain 16 g of 5-decyloxy-2-(4-(4-(hydroxy-1-pentynyl)phenyl)pyrimidine (VIII-1) (yield 78.6%).

Then, 8.5 g (21.3 mmol) of the (VIII-1) thus obtained was mixed with 2.80 g of acetic anhydride and 60 ml of pyridine and stirred at 40°–50° C. for 5 hours.

After completion of the reaction, the reaction mixture was poured into 100 ml of water, neutralized with dilute sulfuric acid and extracted with toluene-ethyl acetate mixture. The organic solvent layer thus obtained was washed with water and concentrated under reduced pressure to obtain 9.3 g (yield 98.3%) of 5-decyloxy-2-(4-(4-acetyl-1-pentynyl)phenyl)pyrimidine (IX-1).

Then, 8.8 g (20 mmol) of (IX-1) thus obtained was added to a mixture of 150 ml of 0.8M phosphate buffer (pH 7.0), 6 ml of chloroform and 1.5 g of Genus Pseudomonas lipase (Lipase Amano PS) and vigorously stirred at 36°–38° C. for 30 hours.

The mixture was extracted with 200 ml of toluene-ethyl acetate mixture, and the organic layer was washed with water and concentrated under reduced pressure.

The mixture thus obtained was separated by silica gel column chromatography using toluene-ethyl acetate mixture as eluent to obtain 3.97 g (yield 47.5%) of (−)-5-decyloxy-2-(4-(4-hydroxy-1-pentynyl)phenyl)pyrimidine (III-1), $[\alpha]_D^{26}=-7.2°$ (c=1, chloroform), mp 71°–72° C., and 4.27 g (yield 48.5%) of (−)-5-decyloxy-2-(4-(4-acetyloxy-1-pentynyl)phenyl)pyrimidine, $[\alpha]_D^{26}=-9.5°$ (c=1, chloroform).

Then, 0.4 g (1 mmol) of (III-1) thus obtained was dissolved in 10 ml of tetrahydrofuran, 0.05 g (1.2 mmol) of potassium hydride was added, the mixture was stirred at room temperature for one hour, 0.23 g (1.5 mmol) of ethyl iodide dissolved in 3 ml of tetrahydrofuran was added, and the resulting mixture was stirred at room temperature for 3 hours.

After completion of the reaction, a small quantity of methanol was added to treat the unreacted potassium hydride, the reaction mixture was poured into 30 ml of water and extracted with 50 ml of ethyl acetate, and the organic layer was washed with water and concentrated under reduced pressure.

The mixture thus obtained was separated by silica gel column chromatography using toluene-ethyl acetate as eluent to obtain 0.38 g (yield 85%) of (−)-5-decyloxy-2-(4-(4-ethoxy-1-pentynyl)phenyl)pyrimidine (I-1), $[\alpha]_D^{26}=-5.8°$ (c=1, chloroform).

Subsequently, 0.21 g (0.5 mmol) of (I-1), 5 ml of ethyl acetate and 0.03 g of 5% palladium-carbon were charged, and hydrogenating reduction was carried out at ordinary pressure at 30° C. The reaction was completed in 2 hours. The catalyst was filtered off, the filtrate was concentrated under reduced pressure, and the concentrate was purified by chromatography using toluene-ethyl acetate to obtain 0.21 g (yield 97%) of (−)-5-decyloxy-2-(4-(4-ethoxy-1-pentyl)phenyl)pyrimidine (II-1).

$[\alpha]_D^{20}=-5.1°$ (c=1, chloroform)

Phase series:  $S_1 \xrightarrow{25} S_c \xrightarrow{54} S_A \xrightarrow{59} I$

EXAMPLE 2

0.4 g (0.1 mmol) of (III-1) obtained in Example 1, 6 g (33 mmol) of butyl iodide and 4 g of silver oxide were charged and reacted at 50° C. for 40 hours. The silver oxide was filtered off and further washed with ethyl acetate sufficiently. The filtrate was concentrated and purified by chromatography to obtain 0.35 g (yield 76%) of (−)-5-decyloxy-2-(4-(4-butoxy-1-pentynyl)phenyl)pyrimidine (I-2).

$[\alpha]_D^{20}=-5.3°$ (c=1, chloroform)

Then, 0.23 g (0.5 mmol) of (I-2) was reduced according to Example 1 to obtain 0.22 g (yield 96%) of (−)-5-decyloxy-2-(4-(4-butoxy-1-pentyl)phenyl)pyrimidine (II-2).

$[\alpha]_D^{20}=-5.0°$ (c=1, chloroform)

EXAMPLE 3

0.4 g (1 mmol) of (III-1) obtained in Example 1 was dissolved in 15 ml of pyridine, 0.2 g of acetyl chloride was added, and the mixture was stirred at 20°–30° C. for 3 hours. After completion of the reaction, the reaction mixture was diluted with 50 ml of ethyl acetate and washed successively with 3N-HCl, water, 5% aqueous sodium bicarbonate solution and water, and the ethyl acetate layer was concentrated under reduced pressure. The residue was purified by chromatography to obtain 0.42 g (yield 96%) of (+)-5-decyloxy-2-(4-(4-acetoxy-1-pentynyl)phenyl)pyrimidine (I-3).

$[\alpha]_D^{20}=+9.8°$ (c=1, chloroform)

Phase series:  $K \xrightarrow{45} S_c \xrightarrow{53} S_A \xrightarrow{66} I$

Then, 0.22 g (0.5 mmol) of (I-3) obtained above, 5 ml of tetrahydrofuran and 0.02 g of 10% palladium-carbon were used to carry out a reduction at a hydrogen pressure of 5 kg/cm$^2$ at 20°–25° C. Subsequently, after-treatment and purification were carried out in the same manner as in Example 1 to obtain 0.21 g (yield 96%) of (+)-5-decyloxy-2-(4-(4-acetoxy-1-pentyl)phenyl)pyrimidine (II-3). $[\alpha]_D^{20}=+7.8°$ (c=1, chloroform)

EXAMPLE 4

0.4 g (1 mmol) of (III-1) obtained in Example 1 was dissolved in 10 ml of dimethylformamide, 0.05 g (1.2 mmol) of potassium hydride was added at 10° C., and the mixture was stirred at room temperature for one hour. Then, 0.52 g (2 mmol) of ethoxypropyl tosylate was added and reacted at 30°–40° C. for 5 hours. After completion of the reaction, after-treatment and purification were carried out in the same manner as in Example 1 to obtain 0.36 g (yield 75%) of (−)-5-decyloxy-2-(4-(4-butoxy-1-pentyl)phenyl)pyrimidine (I-4).

$[\alpha]_D^{20}=-5.3°$ (c=1, chloroform)

Then, 0.24 g (0.5 mmol) of (I-4) obtained above, 5 ml of ethyl acetate, 5 ml of methanol and 0.02 g of 2% platinum-carbon were used to carry out a reduction at a hydrogen pressure of 5 kg/cm$^2$ at 30° C. for 3 hours. Subsequently, after-treatment and purification were carried out in the same manner as in Example 1 to obtain 0.24 g (yield 98%) of (−)-5-decyloxy-2-(4-(4-ethoxypropoxy-1-pentyl)phenyl)pyrimidine (II-4).

$[\alpha]_D^{20}=-4.7°$ (c=1, chloroform)

EXAMPLE 5

2.0 g (5 mmol) of (III-1) obtained in Example 1, 30 ml of ethyl acetate and 0.2 g of 10% palladium-carbon were used to carry out a reduction at 20°–30° C. for 4 hours with stirring in a hydrogen atmosphere of ordinary pressure. After completion of the reaction, the catalyst was filtered off, the filtrate was concentrate and the residue was purified by column chromatography to obtain 1.97 g (yield 98%) of 5-decyloxy-2-(4-(4-hydroxy-1-pentyl)phenyl)pyrimidine (V-1).

Then, 0.06 g (1.5 mmol) of potassium hydride was added to 10 ml of a solution containing 0.4 g (1 mmol) of (V-1) in tetrahydrofuran at 10° C., and the mixture was stirred at 25°–30° C. for 2 hours. Then, 0.48 g (2 mmol) of octyl iodide was added and reacted at 20°–30° C. for 2 hours and thereafter at 50° C. for 4 hours. Subsequently, reaction and after-treatment were carried out in the same manner as in Example 1 to obtain 0.33 g (yield 65%) of (−)-5-decyloxy-2-(4-(4-octyloxy-1-pentyl)phenyl)pyrimidine (II-5).

$[\alpha]_D^{20}=-4.2°$ (c=1, chloroform)

EXAMPLE 6

To a solution consisting of 0.4 g (1 mmol) of (V-1), 5 ml of dichloromethane and 5 ml of pyridine was added 0.39 g (3 mmol) of propionic acid anhydride at 10°–15° C., and the mixture was reacted at 40°–50° C. for 5 hours. After completion of the reaction, the reaction mixture was poured into ice water. After adding 20 ml of dichloromethane, the organic layer was washed with 2N-HCl, water, 5% aqueous solution of sodium bicarbonate and water successively. The organic layer was concentrated under reduced pressure and the concentrate was purified by chromatography to obtain 0.43 g (yield 95%) of (+)-5-decyloxy-2-(4-(4-propionyloxy-1-pentyl)phenyl)pyrimidine (II-6).

$[\alpha]_D^{20}$=+7.3° (c=1, chloroform)

EXAMPLE 7

A four-necked flask equipped with a stirring device and a thermometer was charged with 7.8 g (0.02 mol) of 2-(4-bromophenyl)-5-decyloxypyrimidine, 3.4 g (0.03 mol) of 4-heptyn-6-ol, 0.13 g of bis(triphenylphosphine)-palladium chloride, 0.13 g of copper iodide, 0.26 of triphenylphosphine and 50 ml of triethylamine. The content of the flask was reacted under a stream of nitrogen at 80°–90° C. for 7 hours.

After completion of the reaction, the reaction mixture was poured into 200 ml of water, and extracted with 200 ml of toluene. The toluene layer thus obtained was washed with 3% aqueous HCl and water and concentrated under reduced pressure to obtain a brown colored residue.

The residue was purified by silica gel column chromatography using toluene-ethyl acetate mixture as eluent to obtain 6.4 g (yield 76%) of 2-(4-(6-hydroxy-1-heptynyl)phenyl)-5-decyloxypyrimidine (VIII-2), mp 82°–83° C.

Then, 4.2 g (10 mmol) of the (VIII-2) thus obtained, 2 g of acetic anhydride and 20 ml of pyridine were charged and reacted at 50° C. for 4 hours. After completion of the reaction, the reaction mixture was poured into 50 ml of water, adjusted to pH 3 with 5% aqueous HCl solution, and extracted with 100 ml of toluene. The organic solvent layer thus obtained was washed with water and concentrated under reduced pressure to obtain 4.6 g (yield 99%) of 2-(4-(6-acetoxy-1-heptynyl)phenyl)-5-decyloxypyrimidine (IX-2), mp 57°–58° C.

Then, 4.6 g (10 mmol) of the (IX-2) thus obtained was added to a mixture of 160 ml of 0.3M phosphate buffer (pH 7.0), 10 ml of chloroform and 1.4 g of Genus Pseudomonas lipase (Lipase Amano P) and vigorously stirred at 30°–35° C. for 40 hours.

The mixture was extracted with 200 ml of toluene, and the organic layer was washed with water and concentrated under reduced pressure.

The residue thus obtained was separated by silica gel column chromatography using toluene-ethyl acetate mixture as eluent to obtain 1.8 g (yield 45%) of (−)-2-(4-(6-hydroxy-1-heptynyl)phenyl)-5-decyloxypyrimidine (III-2), $[\alpha]_D^{20}$=−3.3° (c=1, chloroform), and 2.4 g (yield 52%) of (−)-2-(4-(6-acetyloxy-1-heptynyl)phenyl)-5-decyloxypyrimidine, $[\alpha]_D^{20}$=−1.4° (c=1, chloroform).

Then, 0.43 g (1 mmol) of the (III-2) thus obtained was dissolved in a solution consisting of 10 ml of tetrahydrofuran and 1 ml of hexamethylphosphorylamide. Subsequently, 0.05 g (1.2 mmol) of potassium hydride was added thereto at 10° C. or below, the mixture was stirred at room temperature for two hour, 0.22 g (2 mmol) of ethyl bromide was added, and the resulting mixture was reacted at room temperature for 3 hours and thereafter at 40° C. for 3 hours. After completion of the reaction, the product was after-treated and purified in the same manner as in Example 1 to obtain 0.34 g (yield 75%) of (−)-2-(4-(6-ethoxy-1-heptynyl)phenyl)-5-decyloxypyrimidine (I-7). $[\alpha]_D^{20}$=−2.6° (c=1, chloroform).

Then, 0.23 g (0.5 mmol) of the (I-7) thus obtained, 5 ml of methanol, 5 ml of ethyl acetate and 0.03 g of 5% palladium-carbon were used to carried out a reduction at 30° C. under a hydrogen pressure of 5 kg/cm². After completion of the reaction, after-treatment and purification were carried out in the same manner as in Example 1 to obtain 0.22 g (yield 97%) of (−)-2-(4-(6-ethoxy-1-heptynyl)phenyl)-5-decyloxypyrimidine (II-7).

$[\alpha]_D^{20}$=−2.1° (c=1, chloroform)

EXAMPLE 8

0.43 g (1 mmol) of (III-2) obtained above, 5 ml of pyridine and 0.4 g (4 mmol) of acetic anhydride were reacted at 40° C. for 5 hours. After completion of the reaction, the reaction mixture was worked up and purified in the same manner as in Example 6 to obtain 0.45 g (yield 96%) of (+)-2-(4-(6-acetoxy-1-heptynyl)phenyl)-5-decyloxypyrimidine (I-8).

$[\alpha]_D^{20}$+1.7° (c=1, chloroform)

Subsequently, 0.23 g (0.5 mmol) of (I-8) thus obtained was reduced in the same manner as in Example 3 to obtain 0.23 g (yield 96%) of (−)-2-(4-(6-acetoxy-1-heptyl)phenyl)-5-decyloxypyrimidine (II-8).

$[\alpha]_D^{20}$+1.4° (c=1, chloroform)

EXAMPLE 9

18.2 g (0.05 mol) of 6-decyloxy-2-bromo-naphthalene, 10.5 g (0.15 mol) of 3-butyl-2-ol, 0.4 g of copper iodide, 0.7 g of tripheylphosphine, 0.4 g of bis(triphenylphosphine) palladium chloride and 200 ml of triethylamine were charged and stirred at 80° C. for 12 hours in an atmosphere of nitrogen. After completion of the reaction, the reaction mixture was poured into ice-containing aqueous hydrochloric acid and extracted with 200 ml of ethyl acetate. The organic layer was further washed with water and concentrated under reduced pressure.

By purifying the residue by column chromatography, 14.6 g (yield 83%) of 6-decyloxy-2-(3-hydroxy-1-butynyl)naphthalene (VIII-3) was obtained. mp 131°–132° C.

Then, 7.0 g (0.02 mol) of the (VIII-3) thus obtained, 3.9 g (0.03 mol) of propionic acid anhydride, 35 ml of pyridine and 3.5 ml of dimethylaminopyridine were reacted at 30° C. for 5 hours. Subsequently, the reaction mixture was worked up and purified in the same manner as in Example 1 to obtain 8.0 g (yield 98%) of 6-decyloxy-2-(3-propionyloxy-1-butynyl)naphthalene (IX-3). mp 74°–75° C.

Then, a mixed solution consisting of 4.1 g (0.01 mol) of the (IX-3) thus obtained, 120 ml of 0.3M phosphate buffer (pH 7.0), 6 ml of chloroform and 0.8 g of Genus Arthrobacter lipase (manufactured by Shin'nippon Kagaku) was stirred at 35° C. for 50 hours. After the reaction, the reaction mixture was worked up and purified in the same manner as in Example 1 to obtain 1.2 g (yield 35%) of (+)-6-decyloxy-2-(3-hydroxy-1-butynyl)naphthalene (III-3), $[\alpha]_D^{20}$=+15.9° (c=1, chloroform), and 2.5 g (yield 61%) of (−)-6-decyloxy-2-(3-propionyloxy-1-butynyl)naphthalene, $[\alpha]_D^{20}$=−112.5° (c=1, chloroform).

Then, 0.35 g (1 mmol) of (III-3), 0.04 g (1.5 mmol) of sodium hydride and 5 ml of dimethylformamide were charged and stirred at 10°–20° C. for one hour. Subsequently, 0.51 g (3 mmol) of iodopropane was added and reacted at 30°–35° C. for 5 hours. After completion of the reaction, the mixture was worked up in the same manner as in Example 1 and purified to obtain 0.32 g (yield 82%) of (+)-6-decyloxy-2-(3-propoxy-1-butynyl)naphthalene (I-9).

$[\alpha]_D^{20}$=+12.4° (c=1, chloroform)

Then, 0.20 g (0.5 mmol) of (I-8) was reduced in the same manner as in Example 1 to obtain 0.20 g (yield 98%) of (+)-6-decyloxy-2-(3-propoxy-1-butyl)naphthalene (II-9).

$[\alpha]_D^{20}$=+11.9° (c=1, chloroform)

EXAMPLE 10

7.8 g (0.02 mol) of 4-decyloxy-4'-bromobiphenyl, 3.9 g (0.04 mol) of 1-hexin-5-ol, 0.2 g of bis(triphenylphosphine) palladium chloride, 0.25 g of copper iodide, 0.4 g of triphenylphosphine, 30 ml of triethylamine and 10 ml of dimethylformamide were charged and reacted at 80° C. for 10 hours under a stream of nitrogen gas.

After completion of the reaction, the reaction mixture was poured into 100 ml of water, ethyl acetate was added, and the mixture was weakly acidified with 10% aqueous hydrochloric acid. The organic layer was further washed with water and concentrated under reduced pressure, whereby 6.6 g (yield 81%) of 4-decyloxy-4'-(5-hydroxy-1-hexynyl)-biphenyl (VIII-4) was obtained. mp 97°–99° C.

Then, 4.1 g (10 mmol) of (VIII-4) thus obtained, water, 60 ml of dichloromethane and 3.0 g of triethylamine were charged, into which was dropwise added 1.6 g (20 mmol) of acetyl chloride at 0°14 10° C. After the dropping, the mixture was reacted at the same temperature as above for one hour, and thereafter at 25°–30° C. for 4 hours. After completion of the reaction, the reaction mixture was poured into ice water and pH was adjusted to 4.0 with 5% aqueous HCl solution. The organic layer was washed with water and concentrated under reduced pressure to obtain 4.4 g (yield 98.5%) of 4-decyloxy-4'-(5-acetoxy-1-hexynyl)biphenyl (IX-4). mp 80°–82° C.

Then, 2.2 g (5 mmol) of (IX-4) thus obtained, 3 ml of chloroform, 80 ml of 2M phosphate buffer (pH 7.0) and 0.4 g of Genus Arthrobacter lipase (manufactured by Shin'nippon Kagaku) were stirred at 30°–35° C. for 30 hours. After completion of the reaction, the reaction mixture was extracted with ethyl acetate and concentrated under reduced pressure, and the residue was purified by chromatography to obtain 0.9 g (yield 44%) of optically active 4-decyloxy-4'-(5-hydroxy-1-hexynyl)biphenyl (III-4), $[a]_D^{20}$=–2.8° (c=1, chloroform), and 1.2 g (yield 54%) of optically active 4-decyloxy-4'-(5-acetoxy-1-hexynyl)biphenyl, $[\alpha]_D^{20}$=–1.2° (c=1, chloroform).

Then, 0.05 g (1.2 mmol) of potassium hydride was added a solution consisting of 0.41 g (1 mmol) of (III-4) obtained above, 8 ml of tetrahydrofuran and 2 ml of dimethylformamide, and the resulting mixture was stirred at room temperature for one hour. Then, 0.37 g (2 mmol) of butyl iodide was added and the whole mixture was reacted at room temperature for 3 hours and thereafter at 40° C. for 4 hours. Then, work-up treatment and purification were carried out in the same manner as in Example 1 to obtain 0.35 g (yield 75%) of 4-decyloxy-4'-(5-butoxy-1-hexynyl)biphenyl (I-10).

$[\alpha]_D^{20}$=–2.1° (c=1, chloroform)

Then, 0.23 g (0.5 mmol) of (I-10) was catalytically hydrogenated in the same manner as in Example 1 to obtain 0.23 g (yield 98%) of 4-decyloxy-4'-(5-butoxy-1-hexyl)biphenyl (II-10).

$[\alpha]_D^{20}$=–1.9° (c=1, chloroform)

Phase series K —32— Sc* —41— I

EXAMPLE 11

0.41 g (1 mmol) of (III-4) obtained in Example 10, 10 ml of dichloromethane, 2 ml of pyridine and 0.5 g of 4-N,N-dimethylaminopyridine were charged, and then 0.19 g (1.5 mmol) of (–)-α-chloropropionyl chloride was added thereto at 5°–10° C. After maintaining the mixture at the same temperature as above for 3 hours, after-treatment and purification were carried out in the same manner as in Example 3 to obtain 0.45 g (yield 94%) of 4-decyloxy-4'-(5-(α-chloropropionyloxy)-1-hexynyl)biphenyl (I-11).

$[\alpha]_D^{20}$=–3.5° (c=1, chloroform)

By reducing (I-11) in the same manner as above, the following compound is obtained:

4-decyloxy-4'-(5-(α-chloropropionyloxy)-1-hexyl)biphenyl (II-11)

EXAMPLE 12

7.5 g (0.02 mol) of 3-decyl-6-bromophenyl-pyridazine, 5 g (0.04 mol) of 4-acetoxy-1-pentyl, 0.2 g of bis(triphenylphosphine)palladium chloride, 0.2 g of copper iodide, 0.4 g of triphenylphosphine, 20 ml of triethylamine and 20 ml of N-methylpyrrolidone were charged and reacted at 80° C. for 7 hours. After completion of the reaction, work-up treatment and purification were carried out in the same manner as in Example 1 to obtain 7.0 g (yield 83%) of 3-decyl-6-(4-acetoxy-1-pentynyl)phenylpyridazine (IX-5).

Subsequently, 4.2 g (0.01 mol) of (IX-5), 4 ml of chloroform, 200 ml of 3M phosphate buffer (pH 7.0) and 0.4 g of Genus Pseudomonas lipase (Amano P) were vigorously stirred at 35°–40° C. for 40 hours. Thereafter, work-up treatment and purification were carried out in the same manner as in Example 1 to obtain 1.74 g (yield 46%) of (–)-3-decyl-6-(4-hydroxy-1-pentynyl)phenylpyridazine (III-5), $[\alpha]_D^{20}$=–8.3° (c=1, chloroform), and 2.14 g (yield 51%) of optically active 3-decyl-6-(4-acetoxy-1-pentynyl)phenylpyridazne, $[\alpha]_D^{20}$=–13.1° (c=1, chloroform)

Subsequently, 0.05 g (1.2 mmol) of potassium hydride was added to a solution consisting of 0.38 g (1 mmol) of (III-5) and 10 ml of tetrahydrofuran, and reacted with 0.23 g (1.5 mmol) of ethyl iodide in the same manner as in Example 1. Thereafter, work-up treatment and purification were carried out in the same manner as in Example 1 to obtain 0.33 g (yield 81%) of (–)-3-decyl-6-(4-ethoxy-1-pentynyl)phenylpyridazine (I-12).

$[\alpha]_D^{20}$=–6.2° (c=1, chloroform)

Then 0.2 g (0.5 mmol) of (I-12) was reduced with 5% palladium-carbon to obtain 0.2 g (yield 97%) of (–)-3-decyl-6-(4-ethoxy-1-pentyl)phenylpyridazine (II-12).

$[\alpha]_D^{20}$=–5.0° (c=1, chloroform)

EXAMPLE 13

In the same manner as in Example 8, 0.38 g (1 mmol) of (III-5) obtained in Example 12 was acetylated or acetylated and then reduced to obtain the following compounds, respectively:

(–)-3-decyl-6-(4-acetoxy-1-pentynyl)phenylpyridazine (I-13), $[\alpha]_D^{20}$=+14.6° (c=1, chloroform), and (−)-3-decyl-6-(4-acetoxy-1-pentyl)phenylpyridazine (II-13), $[\alpha]_D^{20}$=+12.6° (c=1, chloroform).

EXAMPLES 14–51

In the same manner as in any one of Examples 1–13, each of the starting materials shown in Tables 3 and 4 was reacted and after-treated to obtain the results shown in Tables 3 and 4.

TABLE 3

| Example | Starting alcohol derivative (III) | | | Carboxylic acid or alkylating agent | Acetylene derivative (I) | | $[\alpha]_D^{20}$ c = 1, Chloroform | Compound (II) | | $[\alpha]_D^{20}$ c = 1, Chloroform | Phase series |
|---|---|---|---|---|---|---|---|---|---|---|---|
| | $R^1$ | m | $-A-B-$ | | n | s | $R^2$ | s | $R^2$ | | |
| 14 | $C_{10}H_{21}$ | 1 | pyridine-phenyl | $C_3H_7I$ | 1 | 0 | $C_3H_7$ | −3.8° | 0 | $C_3H_7$ | −3.6° | |
| 15 | $C_{12}H_{25}$ | " | naphthalene | $C_2H_5I$ | 3 | " | $C_2H_5$ | +2.5° | " | $C_2H_5$ | +2.2° | |
| 16 | " | " | " | $C_5H_{11}OSO_2$-C$_6$H$_4$-CH$_3$ | " | " | $C_5H_{11}$ | | " | $C_5H_{11}$ | | |
| 17 | " | " | " | $C_3H_7COCl$ | " | 1 | $C_3H_7$ | +1.9° | 1 | $C_3H_7$ | +1.8° | |
| 18 | $C_{10}H_{21}$ | " | " | $C_8H_{17}OSO_2$-C$_6$H$_4$-CH$_3$ | " | 0 | $C_8H_{17}$ | −1.9° | 0 | $C_8H_{17}$ | −1.7° | |
| 19 | " | " | " | $C_5H_{11}$*CHFCOCl | " | 1 | $C_5H_{11}$*CHF− | +3.2° | 1 | $C_5H_{11}$*CHF− | +2.9° | |
| 20 | " | " | " | (+)$C_2H_5$*CH(CH$_3$)COCl | " | " | $C_2H_5$*CH(CH$_3$)− | | " | $C_2H_5$*CH(CH$_3$)− | | |
| 21 | $C_{10}H_{21}$ | 1 | pyridine-phenyl | (+)cyclopropyl-COCl | 3 | 1 | *cyclopropyl | −8.2° | 1 | *cyclopropyl | −7.8° | |

TABLE 3-continued

| Example | Starting alcohol derivative (III) | | | | Carboxylic acid or alkylating agent | Acetylene derivative (I) | | | Compound (II) | | | |
|---|---|---|---|---|---|---|---|---|---|---|---|---|
| | $R^1$ | m | $-A-B-$ | n | | s | $R^2$ | $[\alpha]^{20}_D$ c=1, Chloroform | s | $R^2$ | $[\alpha]^{20}_D$ c=1, Chloroform | Phase series |
| 22 | = | = | = | = | $C_2H_5\overset{*}{C}H(CH_3)CH_2OSO_2$-C$_6H_4$-CH$_3$ | 0 | $C_2H_5\overset{*}{C}H(CH_3)CH_2-$ | -2.6° | 0 | $C_2H_5\overset{*}{C}H(CH_3)CH_2-$ | -2.4° | |
| 23 | = | = | = | = | $C_2H_5I$ | = | $C_2H_5$ | -2.4° | = | $C_2H_5$ | -2.3° | |
| 24 | = | 0 | = | = | $C_4H_9I$ | = | $C_4H_9$ | | = | $C_4H_9$ | | |
| 25 | = | = | = | = | CH$_2$=CHCH$_2$Cl | = | CH$_2$=CHCH$_2$- | -2.6° | = | $C_3H_7$ | -2.2° | 46° 53°<br>-S$_I$-S$_C$-I |
| 26 | $C_7H_{15}$ | 1 | = | = | $C_4H_9I$ | 1 | $C_4H_9$ | -3.2° | 1 | $C_4H_9$ | -2.8° | |
| 27 | $C_{10}H_{21}$ | = | = | = | CH$_3$COCl | 0 | CH$_3$ | +101° | = | CH$_3$ | +91° | (I)<br>K-S$_I$-S$_C$-S$_A$-I<br>9° 18° 36° 38° |

TABLE 4

| Example | Saturated alcohol derivative (V) R¹ | m | A—B | n | Carboxylic acid or alkylating agent | Compound (II) n | R¹ | |
|---|---|---|---|---|---|---|---|---|
| 28 | $C_{10}H_{21}$ | 1 | 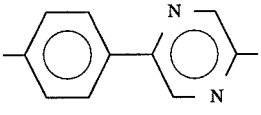 | 3 | $C_4H_9OSO_2$—⬡—$CH_3$ | 0 | $C_4H_9$ | −2.4° |
| 29 | $C_{12}H_{25}$ | 1 | 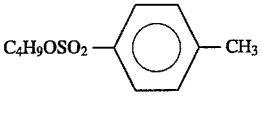 | 3 | $C_4H_9I$ | 0 | $C_4H_9$ | −1.9° |
| 30 | " | " | " | " | $CH_3COCl$ | 1 | $CH_3$ | |
| 31 | $C_8H_{17}$ | " | " | 0 | $C_3H_7I$ | 0 | $C_3H_7$ | −2.5° |
| 32 | $C_{10}H_{21}$ | 1 | 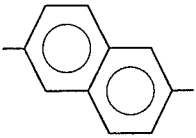 | 3 | $CH_3I$ | 0 | | |
| 33 | " | " | " | " | $C_3H_7COCl$ | 1 | $C_3H_7$ | +1.2° |
| 34 | " | 0 | " | " | $C_3H_7I$ | 0 | $C_3H_7$ | −2.7° |
| 35 | $C_8H_{17}$ | 0 | " | 5 | $CH_3I$ | 0 | $CH_3$ | −1.3° |
| 36 | " | " | " | " | $C_3H_7I$ | 0 | $C_3H_7$ | |
| 37 | $C_{16}H_{33}$ | 1 | " | " | $CH_3I$ | 0 | $CH_3$ | |
| 38 | $C_{10}H_{21}$ | 1 | 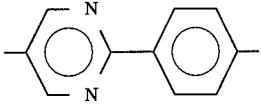 | 1 | $C_5H_{11}OSO_2$—⬡—$CH_3$ | 0 | $C_5H_{11}$ | −3.4° |
| 39 | $C_{12}H_{25}$ | 1 | 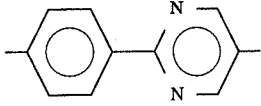 | 3 | $C_2H_5O(CH_2)_3OSO_2$—⬡—$CH_3$ | 0 | $C_2H_5O(CH_2)_3-$ | |
| 40 | $C_5H_{11}$ | 1 | 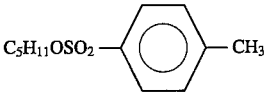 | 3 | $C_4H_9I$ | 0 | $C_4H_9$ | −3.7° |
| | " | " | " | " | $CH_3CH_2COCl$ | 1 | $C_2H_5$ | |

TABLE 5

| Example | R¹ | m | −A−B− | n | Carboxylic acid or alkylating agent |
|---|---|---|---|---|---|
| 41 | $C_{16}H_{33}$ | 1 | pyrimidine-phenylene | 3 | $CH_3COCl$ |
| 42 | " | " | " | " | $CH_3I$ |
| 43 | $C_{10}H_{21}$ | " | phenylene-pyrimidine | 1 | $C_2H_5I$ |
| 44 | " | " | " | 3 | $C_4H_9OSO_2$-C$_6H_4$-$CH_3$ |
| 45 | $C_{12}H_{25}$ | " | biphenylene | " | $C_3H_7Br$ |
| 46 | " | " | " | " | $CH_3COCl$ |
| 47 | $C_{10}H_{21}$ | 0 | quinoxaline | 1 | $C_4H_9I$ |
| 48 | " | " | " | " | $C_3H_7COCl$ |
| 49 | " | " | pyridazine-phenylene | " | $C_2H_5I$ |
| 50 | " | " | " | " | $C_6H_{13}I$ |
| 51 | " | 1 | pyridine-phenylene | 3 | $CH_3COCl$ |
| 52 | " | " | " | " | $C_3H_7I$ |

| | Acetylene derivative (I) | | | Compound (II) | | |
|---|---|---|---|---|---|---|
| Example | s | R² | $[\alpha]_D^{20}$ c = 1, Chloroform | s | R² | $[\alpha]_D^{20}$ c = 1, Chloroform |
| 41 | 1 | $CH_3$ | +1.4° | 1 | $CH_3$ | +1.2° |
| 42 | 0 | $CH_3$ | −2.3° | 0 | $CH_3$ | −2.2° |
| 43 | 0 | $C_2H_5$ | | 0 | $C_2H_5$ | |
| 44 | 0 | $C_4H_9$ | −3.0° | 0 | $C_4H_9$ | −2.8° |
| 45 | 0 | $C_3H_7$ | −1.9° | 0 | $C_3H_7$ | −1.7° |
| 46 | 1 | $CH_3$ | +1.1° | 1 | $CH_3$ | +1.0° |
| 47 | 0 | $C_4H_9$ | | 0 | $C_4H_9$ | |
| 48 | 1 | $C_3H_7$ | | 1 | $C_3H_7$ | |
| 49 | 0 | $C_2H_5$ | −6.1° | 0 | $C_2H_5$ | −5.9° |
| 50 | 0 | $C_6H_{13}$ | −5.0° | 0 | $C_6H_{13}$ | −4.8° |
| 51 | 1 | $CH_3$ | | 1 | $CH_3$ | |
| 52 | 0 | $C_3H_7$ | −2.8° | 0 | $C_3H_7$ | −2.7° |

EXAMPLES 53–54

Using the liquid crystal compounds, the liquid crystal compositions shown in Table 6 were prepared. The compounds were weighed out, heated and melted in a sample bottle and mixed together.

Method for Producing Liquid Crystal Element

A polyimide type polymer film was formed on a glass substrate provided with indium oxide transparent electrode, and rubbed in one direction by means of cotton gauze. A liquid crystal cell was constructed from two glass substrates by using glass fiber having a diameter of 5 μm as a spacer, so that the two substrates became parallel with each other with respect to the direction of rubbing. Then, the above-mentioned composition was sealed into the cell, the liquid crystal element thus formed was combined with a polarizer, an electric field of 20 V was applied, and the change in the intensity of transmitting light was followed. The result demonstrated that this element can be used as a switching element.

palladium chloride, 0.13 g of copper iodide, 0.26 g of triphenylphosphine and 50 ml of triethylamine, and the mixture is reacted at 80°–90° C. for hours under a stream of nitrogen.

After the reaction, the reaction mixture is poured into 200 ml of water and extracted with 200 ml of toluene. The toluene layer thus obtained is washed successively with 3% aqueous HCl solution and water and then concentrated under reduced pressure to obtain a brown-colored residue.

The residue is purified by silica gel column chromatography using toluene-ethyl acetate as eluent to obtain 64 g (yield 76%) of 2-(4-(6-hydroxy-1-heptynyl)phenyl)-5-decyloxypyrimidine (VIII-1), mp 82°–83° C.

Then, 4.2 g (10 mmol) of the (VIII-1) thus obtained, 2 g of acetic anhydride and 20 ml of pyridine are charged and reacted at 50° C. for 4 hours.

After completion of the reaction, the reaction mixture is poured into 50 ml of water, adjusted to pH 3 with 5% aqueous HCl solution, and extracted with 100 ml of toluene. The organic layer is washed with water and concentrated under reduced pressure to obtain 4.6 g (yield 99%) of 2-(4-(6-acetoxy-1-heptynyl)phenyl)-5-decyloxypyrimidine (IX-1), mp 57°–58° C.

Then, 2.3 g (5 mmol) of the (IX-1) thus obtained is dissolved in a mixture consisting of 80 ml of 0.3M phosphate buffer (pH 7.0), 5 ml of chloroform and 0.7 g of Genus

TABLE 6

Example 53

(Compound of Example 7)

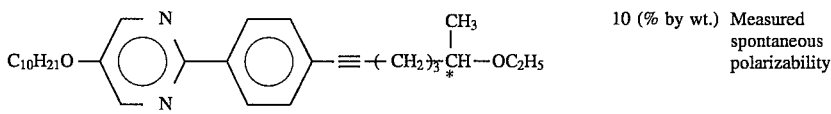

10 (% by wt.)  Measured spontaneous polarizability (Compound of Example 1)

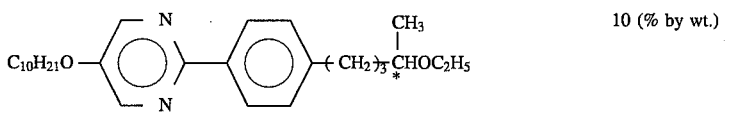

10 (% by wt.)

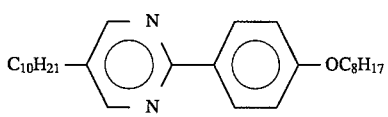

30 (% by wt.) 7 nc/cm²

(Known compound) (I)

50 (% by wt.) (T – Tc = –10° C.)

(Known compound) (II)

Example 54

(Compound of Example 3)

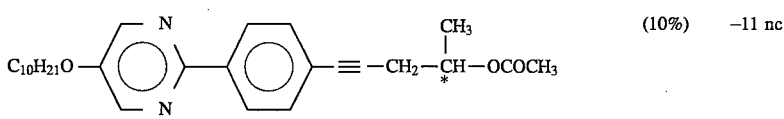

(10%)  –11 nc (Known compound) (I)  (30%)
(Known compound) (II)  (60%)

Referential Example 1

A four-necked flask equipped with a stirring device and a thermometer is charged with 7.8 g (0.02 mol) of 2-(4-bromophenyl)-5-decyloxypyrimidine (VI-1), 0.03 mol of 1-heptyn-6-ol (VII-1), 0.13 g of bis(triphenylphosphine)-

Pseudomonas lipase (Lipase Amano PS) and vigorously stirred at 30°–35° C. for 40 hours.

The mixture is extracted with 100 ml of toluene, and the organic layer is washed with water and concentrated under reduced pressure.

The residue is separated by column chromatography using toluene-ethyl acetate to obtain 0.9 g (yield 45%) of (–)-2-{4-(6-hydroxy-1-heptynyl)phenyl}-5-decyloxypyrimidine (III-1), $[\alpha]_D^{20}$=–3.3° (c=1, chloroform), and 1.2 g (yield 52%) of (–)-2-{4-(6-acetoxy-1-heptynyl)phenyl}-5-decyloxypyrimidine, $[\alpha]_D^{20}$=–1.4° (c=1, chloroform).

Referential Example 2

A mixed solution consisting of 2.1 g (5 mmol) of 2-4-(6-hydroxy-1-heptynyl)phenyl)-5-decyloxypyrimidine (VIII-1), 5 ml of methanol, 20 ml of ethyl acetate and 0.2 g of 5% palladium-carbon is hydrogenated at 35°–40° C. under a hydrogen pressure of 10 kg/cm². After completion of the reaction, the catalyst is filtered off, and the filtrate is concentrated under reduced pressure to obtain 2.1 g (yield 98.5%) of 2-(4-(6-hydroxy-1-heptyl)phenyl)-5-decyloxypyrimidine (XIV-2), mp 78°–79° C.

Then, 1.7 g (4 mmol) of the (XIV-2), 2 g of triethylamine and 30 g of dichloromethane are charged, and 0.5 g (6 mmol) of acetyl chloride is added thereto at a temperature not higher than 10° C. The resulting mixture is reacted at this temperature for one hour, and then at 20°–30° C. for 2 hours. After completion of the reaction, the reaction mixture is poured into ice water, and the organic layer is separated, washed with 3% aqueous hydrochloric acid, water, 3% sodium bicarbonate solution and water successively, and concentrated. Purification of the residue by column chromatography gives 1.8 g (yield 98%) of 2-(4-(6-acetoxy-1-heptyl)phenyl)-5-decyloxypyrimidine (XII-2), mp 72°–73° C.

Then, a mixture consisting of 1.4 g (3 mmol) of the (XII-2), 40 ml of 0.2M phosphate buffer (pH 7.5), 2 ml of toluene and 0.36 g of Genus Pseudomonas lipase is stirred at 20°–25° C. for 24 hours.

Subsequently, after-treatment and purification are carried out in the same manner as in Referential Example 1 to obtain 0.5 g (yield 43%) of 2-(4-(6-hydroxy-1-heptyl)phenyl)-5-decyloxypyrimidine (V-2), $[\alpha]_D^{20}$=–2.7° (c=1, chloroform), and 0.8 g (yield 55%) of 2-(4-(6-acetoxy-1-heptyl)phenyl)-5-decyloxypyrimidine, $[\alpha]_D^{20}$=–1.1° (c=1, chloroform).

Referential Example 3

A mixed solution consisting of 0.84 g (2 mmol) of the optically active 2-(4-(6-hydroxy-1-heptynyl)phenyl)-5-decyloxypyrimidine (III-1) obtained in Referential Example 1, 3 ml of methanol, 10 ml of THF and 0.1 g of 5% palladium-carbon is hydrogenated at 30°–35° C. under a hydrogen pressure of 5 kg/cm². The same work-up treatment and purification as in Referential Example 2 give 0.83 g (yield 98%) of optically active 2-(4-(6-hydroxy-1-heptyl)phenyl)-5-decyloxypyrimidine (V-3), $[\alpha]_D^{20}$=–2.8° (c=1, CHCl3).

In the same manner as above, 0.92 g (yield 98.5%) of 2-(4-(6-acetoxy-1-heptyl)phenyl)-5-decyloxypyrimidine, $[\alpha]_D^{20}$=–1.2° (c=1, chloroform), is obtained from 0.93 g of optically active 2-(4-(6-acetoxy-1-heptynyl)phenyl)-5-decyloxypyrimidine.

Referential Example 4

A four-necked flask equipped with a stirring device and a thermometer is charged with 7.3 g (0.02 mol) of 2-(4-bromophenyl)-5-octyloxypyrimidine (VI-4), 6.2 g (0.04 mol) of 6-acetoxy-1-heptyne, 0.15 g of bis(triphenylphosphine)-palladium chloride, 0.15 g of copper iodide, 0.29 g of triphenylphosphine and 50 ml of diethylamine. The mixture is reacted under reflux for 9 hours under a stream of nitrogen gas.

After completion of the reaction, work-up treatment and purification are carried out in the same manner as in Referential Example 1 to obtain 6.8 g (yield 78%) of 2-(4-(6-acetoxy-1-heptynyl)phenyl)-5-octyloxypyrimidine (IX-4), mp 58°–59° C.

Then, a mixture consisting of 2.18 g (5 mmol) of the (IX-4) thus obtained, 50 ml of 0.2M phosphate buffer (pH 7.5), 3 ml of dichloromethane and 0.3 g of Genus Pseudomonas lipase (Lipase Amano PS) is vigorously stirred at 35°–40° C. for 30 hours. The reaction mixture is extracted with 100 ml of ethyl acetate, and the organic layer is washed with water and concentrated under reduced pressure.

The residue is separated by silica gel column chromatography using toluene-ethyl acetate as eluent to obtain 0.91 g (yield 46%) of (–)-2-(4-(6-hydroxy-1-heptynyl)phenyl)-5-octyloxypyrimidine (III-4), $[\alpha]_D^{20}$=–2.8° (c=1, chloroform), and 1.13 g (yield 52%) of (–)-2-(4-(6-acetoxy-1-heptynyl)phenyl)-5-octyloxypyrimidine, $[\alpha]_D^{20}$=–1.2° (c=1, chloroform).

If reduced in the same manner as in Referential Example 3, the compound (III-4) and optical active ester derivative obtained herein give optically active 2-(4-(6-hydroxy-1-heptyl)-phenyl)-5-octyloxypyrimidine (V-4) and optically active 2-(4-(6-acetoxy-1-heptyl)phenyl)-5-octyloxypyrimidine, respectively.

Referential Example 5

A mixed solution consisting of 4.4 g (0.01 mol) of 2-(4-(6-acetoxy-1-heptynyl)phenyl)-5-octyloxypyrimidine (IX-4) obtained in Referential Example 4, 40 ml of ethyl acetate and 0.46 g of 5% palladium-carbon is hydrogenated under normal pressure at 20°–25° C. By filtering off the catalyst and concentrating the filtrate, 4.4 g (yield 99%) of 2-(4-(6-acetoxy-1-heptyl)phenyl)-5-octyloxypyrimidine (XII-5), mp 73°–74° C., is obtained.

Then, a mixture consisting of 2.2 g (5 mmol) of (XII-5) obtained above, 60 ml of 0.2M phosphate buffer (pH 7.0) and 0.3 g of Genus Pseudomonas lipase (Lipase Amano P) is vigorously stirred at 30°–35° C. for 30 hours.

Thereafter, work-up treatment and purification are carried out in the same manner as in Referential Example 4 to obtain 0.84 g (yield 42%) of optically active 2-(4-(6-hydroxy-1-heptyl)phenyl)-5-octyloxypyrimidine (V-5), $[\alpha]_D^{20}$=–2.3° (c=1, chloroform), and 1.23 g (yield 56%) of 2-(4-(6-acetoxy-1-heptyl)phenyl)-5-octyloxypyrimidine, $[\alpha]_D^{20}$=–1.1° (c=1, chloroform).

Referential Example 6

18.2 g (0.05 mol) of 6-decyloxy-2-bromo-naphthalene (VI-6), 10.5 g (0.15 mol) of 3-butyn-2-ol, 0.4 g of copper iodide, 0.7 g of triphenylphosphine, 0.4 g of bis(triphenylphosphine)-palladium chloride and 100 ml of diethylamine are charged and stirred for 12 hours under reflux in an atmosphere of nitrogen. After completion of the reaction, the reaction mixture is poured into ice-containing aqueous hydrochloric acid and extracted with 200 ml of ethyl acetate. The organic layer is further washed with water and concentrated under reduced pressure.

The residue thus obtained is purified by column chromatography to obtain 14.6 g (yield 83%) of 6-decyloxy-2-(3-hydroxy-1-butynyl)naphthalene (VIII-6), mp 131°–132° C.

Then, 7.0 g (0.02 mol) of the (VIII-6) obtained above, 3.9 g (0.03 mol) of propionic anhydride, 35 ml of pyridine and 3.5 ml of dimethylaminopyridine are charged and reacted at 30° C. for 5 hours. Thereafter, work-up treatment and purification are carried out in the same manner as in Referential Example 1 to obtain 8.0 g (yield 98%) of 6-decyloxy-2-(3-propionyloxy-1-butynyl)naphthalene (IX-6), mp 74°–75° C.

Then, a mixed solution consisting of 4.1 g (0.01 mol) of the (IX-6) obtained above, 20 ml of 0.3M phosphate buffer (pH 7.0), 6 ml of chloroform and 0.8 g of Genus Arthrobacter lipase (manufactured by Shin'nippon Kagaku) is stirred at 35° C. for 50 hours. After completion of the reaction, work-up treatment and purification are carried out in the same manner as in Referential Example 1 to obtain 1.2 g (yield 35%) of 6-decyloxy-2-(3-hydroxy-1-butynyl)naphthalene (III-6), $[\alpha]_D^{20}=+15.9°$ (c=1, chloroform), and 2.5 g (yield 61%) of 6-decyloxy-2-(3-propionyloxy-1-butynyl)naphthalene, $[\alpha]_D^{20}=-112.5°$ (c=1, chloroform).

Then, 1.1 g (3 mmol) of the optically active 6-decyloxy-2-(3-hydroxy-1-butynyl)naphthalene (III-6) obtained above, 11 ml of tetrahydrofuran (THF) and 0.11 g of 5% palladium-carbon are hydrogenated under normal pressure. The reaction is completed in 4 hours at 20° C. After filtering off the catalyst, the filtrate is concentrated and the concentrate is purified by chromatography to obtain 1.0 g (yield 98%) of 6-decyloxy-2-(3-hydroxy-1-butyl)naphthalene (V-6), $[\alpha]_D^{20}=-7.8°$ (c=1, chloroform).

In the same manner as above, 1.2 g (yield 98.5%) of 6-decyloxy-2-(3-propionyloxy-1-butyl)naphthalene, $[\alpha]_D^{20}=-12.8°$ (c=1, chloroform), is obtained from 1.2 g (3 mmol) of optically active 6-decyloxy-2-(3-propionyloxy-1-butynyl)naphthalene.

Referential Example 7

A four-necked flask equipped with a stirring device and a thermometer is charged with 20 g (51.1 mmol) of 2-(4-bromophenyl)-5-decyloxypyrimidine (VI-7), 12.9 g (153 mmol) of 4-pentyn-2-ol, 0.34 g (1.78 mmol) of copper iodide, 0.67 g (2.55 mmol) of triphenylphosphine, 0.34 g of bis(triphenyl-phosphine) palladium (II) chloride and 200 ml of triethylamine and heated and stirred at 90° C. for 8 hours in an atmosphere of nitrogen.

After completion of the reaction, the reaction mixture is poured into 200 ml of water, neutralized with dilute sulfuric acid and extracted with toluene-ethyl acetate mixture. The organic layer is washed with water and concentrated under reduced pressure to obtain a yellow-brown colored residue.

Purification of the residue by silica gel column chromatography using toluene-ethyl acetate as eluent gives 16.0 g (yield 78.6%) of 5-decyloxy-2-{(4-hydroxy-1-pentynyl)phenyl}pyrimidine (VIII-7).

Then, 8.5 g (21.3 mmol) of the (VIII-7) obtained above, 2.80 g of acetic anhydride and 60 ml of pyridine are charged and stirred at 40°–50° C. for 5 hours.

After completion of the reaction, the reaction mixture is poured into 100 ml of water, neutralized with dilute sulfuric acid, and extracted with toluene-ethyl acetate mixture. The organic layer is washed with water and concentrated under reduced pressure to obtain 9.3 g (yield 98.3%) of 5-decyloxy-2-((4-acetyl-1-pentynyl)phenyl)-pyrimidine (IX-7).

Then, 8.8 g (20 mmol) of the (IX-7) obtained above is added to a mixture of 150 ml of 0.8M phosphate buffer (pH 7.0), 6 ml of chloroform and 1.5 g of Genus Pseudomonas lipase (Lipase Amano PS) and vigorously stirred at 36°–38° C. for 30 hours.

The resulting mixture is extracted with 200 ml of toluene-ethyl acetate, and the organic layer is washed with water and concentrated under reduced pressure.

The mixed product thus obtained is separated by silica gel column chromatography using toluene-ethyl acetate as eluent to obtain 3.79 g (yield 47.5%) of (−)-5-decyloxy-2-{(4-hydroxy-1-pentynyl)phenyl}pyrimidine (III-7), $[\alpha]_D^{26}=-7.2°$ (c=1, chloroform), mp 71°–72° C., and 4.27 g (yield 48.5%) of (−)-5-decyloxy-2-{(4-acetyloxy-1-pentynyl)phenyl}pyrimidine, $[\alpha]_D^{26}=-9.5°$ (c=1, chloroform).

When reduced in the same manner as in Referential Example 3, the optically active (III-7) and 5-decyloxy-2-((4-hydroxy-1-pentyl)phenyl)pyrimidine obtained herein give the following compounds, respectively:

5-(decyloxy)-2-((4-hydroxypentyl)phenyl)pyrimidine (8-4), $[\alpha]_D^{25}=-3.3°$ (c=1, chloroform), and 5-decyloxy-2-((4-acetoxypentyl)phenyl)pyrimidine.

Referential Example 8

7.8 g (0.02 mol) of 4-decyloxy-4'-bromobiphenyl (VI-8), 3.9 g (0.04 mol) of 1-hexyn-5-ol, 0.2 g of bis(triphenylphosphine)-palladium chloride, 0.25 g of copper iodide, 0.4 g of triphenylphosphine, 30 ml of triethylamine and 10 ml of dimethylformamide are charged and reacted at 80° C. for 10 hours under a stream of nitrogen gas.

After completion of the reaction, the reaction mixture is poured into 100 ml of water, ethyl acetate is added, and the mixture is weakly acidified with 10% aqueous hydrochloric acid. After separating the mixture into phases, the organic layer is washed with water and concentrated under reduced pressure to obtain 6.6 g (yield 81%) of 4-decyloxy-4'-(5-hydroxy-1-hexinyl)biphenyl (VIII-8), mp 97°–99° C.

Then, 60 ml of dichloromethane and 3.0 g of triethylamine are added to 4.1 g (10 mmol) of the (VIII-8) obtained above, to which is dropwise added 1.6 g (20 mmol) of acetyl chloride at 0°–10° C. After the dropping, the resulting mixture is reacted at the same temperature as above for one hour and thereafter at 25°–30° C. for 4 hours. After completion of the reaction, the reaction mixture is poured into ice water, and pH is adjusted to 4.0 with 5% aqueous HCl solution. The organic layer is washed with water and concentrated under reduced pressure to obtain 4.4 g (yield 98.5 %) of 4-decyloxy-4'-(5-acetoxy-1-hexinyl)biphenyl (IX-8), mp 80°–82° C.

Then, 2.2 g (5 mmol) of the (IX-8) obtained above, 3 ml of chloroform, 80 ml of 2M phosphate buffer (pH 7.0) and 0.4 g of Genus Arthrobacter lipase (manufactured by Shin'nippon Kagaku) are stirred at 30°–35° C. for 30 hours. After completion of the reaction, the reaction mixture is extracted with ethyl acetate and concentrated under reduced pressure. The residue is purified by chromatography to obtain 0.9 g (yield 44%) of optically active 4-decyloxy-4'-(5-hydroxy-1-hexinyl)biphenyl (III-8), $[\alpha]_D^{20}=-2.8°$ (c=1, $CHCl_3$), and 1.2 g (yield 54%) of optically active 4-decyloxy-4'-(5-acetoxy-1-hexinyl)biphenyl, $[\alpha]_D^{20}=-1.2°$ (c=1, $CHCl_3$).

When reduced in the same manner as in Referential Example 3, the optically active (III-8) and ester derivative give the following optically active compounds, respectively:

optically active 4-decyloxy-4'-(5-hydroxy-1-hexyl)biphenyl (8-5), $[\alpha]_D^{20}=-2.3°$ (c=1, chloroform), and optically active 4-decyloxy-4'-(5-acetoxy-1-hexyl)biphenyl, $[\alpha]_D^{20}=-1.0°$ (c=1, chloroform).

Referential Example 9

2.0 g (5 mmol) of 4-decyloxy-4'-(5-hydroxy-1-hexynyl)biphenyl (VIII-8) obtained in Referential Example 8 is dissolved in a mixture of 20 ml of ethyl acetate and 10 ml of THF and reduced with hydrogen with 0.2 g of 5% Pd-carbon at 30° C. for 6 hours. After completion of the reaction, the catalyst is filtered off and the filtrate is concentrated under reduced pressure to obtain 2 g (yield 99%) of 4-decyloxy-4'-(5-hydroxy-1-hexyl)biphenyl (XIV-9), mp 92°–93° C.

Then, 1.6 g (4 mmol) of the (XIV-9) thus obtained is acetylated with 1 g of acetic anhydride and 10 ml of pyridine at 50° C. over a period of 4 hours. The same work-up treatment and purification as in Referential Example 1 give 1.8 g (yield 98%) of 4-decyloxy-4'-(5-acetoxy-1-hexyl)biphenyl (XII-9), mp 75°–76° C.

Then, 1.4 g (3 mmol) of the (XII-9) obtained above, 2 ml of chloroform, 60 ml of 2M phosphate buffer (pH 7.0) and 0.2 g of Genus Arthrobacter lipase (manufactured by Shin'nippon Kagaku) are stirred at 30°–40° C. for 30 hours. Thereafter, work-up treatment and purification are carried out in the same manner as in Referential Example 8 to obtain 0.5 g (yield 40%) of optically active 4-decyloxy-4'-(5-hydroxy-1-hexyl)biphenyl (V-9), $[\alpha]_D^{20}=-2.2°$ (c=1, chloroform), and 0.8 g (yield 57%) of optically active 4-decyloxy-4'-(5-acetoxy-1-hexyl)biphenyl, $[\alpha]_D^{20}=-1.1°$ (c=1, chloroform).

Referential Example 10

7.5 g (0.02 mol) of 3-decyl-6-bromophenylpyridazine (VI-10), 5 g (0.04 mol) of 4-acetoxy-1-pentyne, 0.2 g of bis(triphenylphosphine)-palladium chloride, 0.2 g of copper iodide, 0.4 g of triphenylphosphine, 20 ml of triethylamine and 20 ml of N-methylpyrrolidone are charged and reacted at 80° C. for 7 hours.

After completion of the reaction, work-up treatment and purification are carried out in the same manner as in Referential Example 1 to obtain 7.0 g (yield 83%) of 3-decyl-6-(4-acetoxy-1-pentynyl)phenylpyridazine (IX-10).

Then, 4.2 g (0.01 mol) of (IX-10) obtained above, 20 ml of methanol, 20 ml of ethyl acetate and 0.1 g of 2% platinum-carbon are reduced under a hydrogen pressure of 10 kg/cm² at 25°–30° C.

After completion of the reaction, the catalyst is filtered off, and the filtrate is concentrated to obtain 4.2 g (yield 99%) of 3-decyl-6-(4-acetoxy-1-pentyl)phenylpyridazine (XII-10).

Then, 2.1 g (5 mmol) of the (XII-10), 2 ml of dichloromethane, 100 ml of 3M phosphate buffer (pH 7.0) and 0.2 g of Genus Pseudomonas lipase (Amano P) are vigorously stirred for 30 hours at 35°–40° C. Thereafter, work-up treatment and purification are carried out in the same manner as in Referential Example 5 to obtain 0.9 g (yield 47%) of optically active 3-decyl-6-(4-hydroxy-1-pentyl)phenylpyridazine (V-10), mp 84°–85° C., and 1.1 g (yield 51%) of optically active 3-decyl-6-(4-acetoxy-1-pentyl)phenylpyridazine, mp 68°–69° C.

On the other hand, 2.1 g (5 mmol) of the (IX-10) obtained previously can also be converted to the following compounds by asymmetrically hydrolyzing, after-treating and purifying it under the same conditions as above:

0.8 g (yield 43%) of optically active 3-decyl-6-(4-hydroxy-1-pentynyl)phenylpyridazine (III-10), $[\alpha]_D^{20}=-8.5°$ (c=1, chloroform); and 1.2 g (yield 55%) of optically active 3-decyl-6-(4-acetoxy-1-pentynyl)phenylpyridazine, $[\alpha]_D^{20}=-12.6°$ (c=1, chloroform).

Referential Examples 11–19

The optically active alcohol derivatives (III) and optically active saturated alcohols (V) shown in Table 7 can be obtained by successively repeating the reaction and work-up treatment of Referential Example 4, except that the starting materials shown in Table 7 are used.

TABLE 7

| Referential Example | Starting compound | | | Ester derivative (IX) | | | | Optically active alcohol derivative (III) | | Optically active saturated alcohol derivative (V) |
|---|---|---|---|---|---|---|---|---|---|---|
| | Halide (VI) | Acetylene (XI) | $R_0^1$ | m | A—B | n | $R^2$ | Yield of asymmetric hydrolysis | $[\alpha]_D^{20}$ c = 1, CHCl$_3$ | $[\alpha]_D^{20}$ c = 1, CHCl$_3$ |
| 11 | $C_{16}H_{33}O$—⟨⟩—⟨N=N⟩—Br | CH≡C—(CH$_2$)$_3$—CH(CH$_3$)—OCOCH$_3$ | $C_{16}H_{33}$ | 1 | ⟨N=N⟩—⟨⟩ | 3 | CH$_3$ | 41 | −3.1° | −2.9° |
| 12 | $C_7H_{15}O$—⟨⟩—⟨N=N⟩—Br | CH≡C—CH$_2$—CH(CH$_3$)—OCOCH$_3$ | $C_7H_{15}$ | 1 | ⟨N=N⟩—⟨⟩ | 1 | CH$_3$ | 49 | −3.4° | −3.1° |
| 13 | $C_{10}H_{21}O$—⟨⟩—⟨N=N⟩—I | CH≡C—(CH$_2$)$_3$CH(CH$_3$)CHOCOCH$_3$ | $C_{10}H_{21}$ | 1 | ⟨N=N⟩—⟨⟩ | 3 | CH$_3$ | 48 | −3.2° | −2.9° |
| 14 | $C_{10}H_{21}$—⟨N=N⟩—Br | CH≡C—(CH$_2$)$_3$CH(CH$_3$)—OCOCH$_3$ | $C_{10}H_{21}$ | 0 | ⟨N=N⟩—⟨⟩ | 3 | CH$_3$ | 48 | −3.5° | −3.3° |
| 15 | $C_{10}H_{21}O$—⟨⟩—⟨N=N⟩—Br | CH≡C—CH$_2$—CH(CH$_3$)—OCOCH$_3$ | $C_{10}H_{21}$ | 1 | ⟨⟩—⟨N=N⟩ | 1 | CH$_3$ | 48 | −3.3° | −2.9° |
| 16 | $C_{12}H_{25}O$—⟨⟩—⟨N=N⟩—Br | CH≡C—CH(CH$_3$)—OCOCH$_3$ | $C_{12}H_{25}$ | 1 | ⟨N=N⟩ | 0 | CH$_3$ | 44 | +14.8° | −7.7° |
| 17 | $C_{12}H_{25}O$—⟨naphthalene⟩—Br | CH≡C—(CH$_2$)$_3$—CH(CH$_3$)—CHOCOCH$_3$ | $C_{12}H_{25}$ | 1 | ⟨naphthalene⟩ | 3 | CH$_3$ | 45 | −2.8° | −2.5° |

TABLE 7-continued

| Referential Example | Starting compound | | Ester derivative (IX) | | | | Optically active alcohol derivative (III) | | Optically active saturated alcohol derivative (V) |
|---|---|---|---|---|---|---|---|---|---|
| | Halide (VI) | Acetylene (XI) | $R_0^1$ | m | A—B | n | $R^2$ | Yield of asymmetric hydrolysis | $[\alpha]_D^{20}$ c = 1, CHCl$_3$ | $[\alpha]_D^{20}$ c = 1, CHCl$_3$ |
| 18 | $C_{12}H_{25}O$—⟨⟩—⟨⟩—Br | CH≡C(CH$_2$)$_3$—CH(CH$_3$)OCOCH$_3$ | $C_{12}H_{25}$ | 1 | ⟨⟩—⟨⟩ | 3 | CH$_3$ | 44 | −3.1° | −2.8° |
| 19 | $C_{10}H_{21}$—(pyrazine)—Br | CH≡C—(CH$_2$)—CH(CH$_3$)OCOCH$_3$ | $C_{10}H_{21}$ | 0 | (pyrazine) | 1 | CH$_3$ | 46 | −3.0° | −2.9° |

Referential Examples 20–23

The optically active saturated alcohols (V) shown in Table 8 can be obtained by successively repeating the reaction and after-treatment of Referential Example 9, except that the starting materials shown in Table 8 are used.

TABLE 8

| Referential Example | Starting compound | | Alcohol derivative (VIII) | | | | Saturated alcohol (XIV) Yield | Ester (XII) Yield | Yield of asymmetric hydrolysis | Optically active saturated alcohol derivative (V) | | |
|---|---|---|---|---|---|---|---|---|---|---|---|---|
| | Halide (VI) | Acetylene (VII) | $R^1$ | m | A—B | n | | | | $[\alpha]_D^{20}$ c = 1, CHCl$_3$ | $R_1$, A—B, m, n | |
| 20 | $C_8H_{17}O$—(pyrimidine)—(phenyl)—Br | ≡—CH(CH$_3$)—OH | $C_8H_{17}$ | 1 | (pyrimidine)—(phenyl) | 0 | 98% | 98% | 49% | −8.0° | The same as in alcohol derivative (VIII) |
| 21 | $C_9H_{19}$—(pyrimidine)—(phenyl)—Br | ≡—(CH$_2$)$_2$CH(CH$_3$)—OH | $C_9H_{19}$ | 0 | (pyrimidine)—(phenyl) | 2 | 99% | 99% | 47% | −3.0° | The same as in alcohol derivative (VIII) |
| 22 | $C_{10}H_{21}O$—(phenyl)—(pyrimidine)—Br | ≡—(CH$_2$)$_3$CH(CH$_3$)OH | $C_{10}H_{21}$ | 1 | (phenyl)—(pyrimidine) | 3 | 98.5% | 99% | 45% | −2.8° | The same as in alcohol derivative (VIII) |
| 23 | $C_5H_{11}O$—(phenyl)—(phenyl)—Br | ≡—(CH$_2$)$_5$CH(CH$_3$)—OH | $C_5H_{11}$ | 1 | (phenyl)—(phenyl) | 5 | 99% | 98% | 44% | −2.9° | The same as in alcohol derivative (VIII) |

Referential Examples 24–30

The optically active alcohol derivatives (III) and optically active saturated alcohols (V) shown in Table 9 can be obtained by successively repeating the reaction and work-up treatment of Referential Examples 5 and 7, except that the starting materials shown in Table 9 are used.

TABLE 9

| Referential Example | Starting compound | |
|---|---|---|
| | Halide (VI) | Acetylene (VII) or (XI) |
| 24 | C₁₀H₂₁—O—⟨pyridine⟩—⟨phenyl⟩—Br | ≡—(CH₂)₃—CH(CH₃)OH |
| 25 | C₈H₁₇—⟨pyrimidine⟩—⟨phenyl⟩—Br | ≡—(CH₂)₅—CH(CH₅)OCOCH₃ |
| 26 | C₁₀H₂₁—⟨pyridazine⟩—⟨phenyl⟩—Br | ≡—CH₂—CH(CH₃)—OCOCH₃ |
| 27 | C₈H₁₇O—⟨naphthalene⟩—Br | ≡—(CH₂)₄—CH(CH₃)—OH |
| 28 | C₅H₁₁O—⟨phenyl⟩—⟨pyrimidine⟩—Br | ≡—(CH₂)₃—CH(CH₃)OCOCH₃ |
| 29 | " | ≡—(CH₂)₃CH(CH₃)—OH |
| 30 | C₁₀H₂₁O—⟨phenyl⟩—⟨pyridine⟩—Br | ≡—CH₂—CH(CH₃)—OH |

| | Alcohol derivative (VIII) | | | | Ester derivative (IX) | | | |
|---|---|---|---|---|---|---|---|---|
| | R₁ | m | A—B | n | R₁ | m | A—B | n |
| 24 | C₁₀H₂₁ | 1 | ⟨pyridine-phenyl⟩ | 3 | C₁₀H₂₁ | 1 | ⟨pyridine-phenyl⟩ | 3 |
| 25 | | | | | C₈H₁₇ | 0 | ⟨pyrimidine-phenyl⟩ | 5 |
| 26 | | | | | C₁₀H₂₁ | 0 | ⟨pyridazine-phenyl⟩ | 1 |

TABLE 9-continued

| Referential Example | R₁ | m | A—B | n | R₁ | m | A—B | n |
|---|---|---|---|---|---|---|---|---|
| 27 | C₈H₁₇ | 1 | 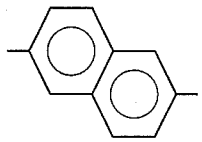 | 4 | C₈H₁₇ | 1 | 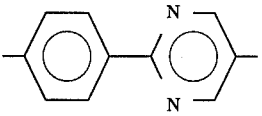 | 4 |
| 28 | | | | | C₅H₁₁ | 1 | 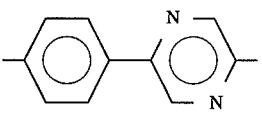 | 3 |
| 29 | C₅H₁₁ | 1 | 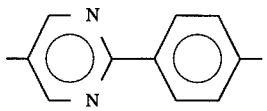 | 3 | C₅H₁₁ | 1 | 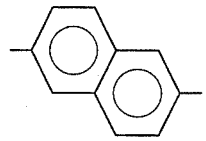 | 3 |
| 30 | C₁₀H₂₁ | 1 | 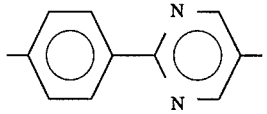 | 1 | C₁₀H₂₁ | 1 | 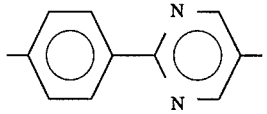 | 1 |

|  | Ester (XII) | | | | Optically active alcohol derivative (III) | |
|---|---|---|---|---|---|---|
|  | $R_1$ | m | A—B | n | Yield of asymmetric hydrolysis | $[\alpha]_D^{20}$ c = 1, CHCl₃ |
| 24 | | | | | 45 | −3.1° |
| 25 | C₈H₁₇ | 0 | (pyrimidine-phenyl) | 5 | | |
| 26 | | | | | 40 | −3.3° |
| 27 | C₈H₁₇ | 1 | (naphthyl) | 4 | | |
| 28 | C₅H₁₁ | 1 | (phenyl-pyrimidine) | 3 | | |
| 29 | | | | | 46 | −2.5° |
| 30 | | | | | 45 | −3.8° |

| | Optically active saturated alcohol derivative (V) | | |
|---|---|---|---|
| | Yield of assymmetric hydrolysis | $[\alpha]_D^{20}$ c = 1, CHCl₃ | Similar Ref. Example |
| 24 | — | −2.9° | 7 |
| 25 | 44 | −2.1° | 5 |
| 26 | — | −3.2° | 7 |
| 27 | 46 | −2.6° | 5 |
| 28 | 45 | −2.7° | 5 |
| 29 | — | −2.3° | 7 |
| 30 | — | −3.3° | 7 |

Referential Example 31

1.9 g (4 mmol) of (IX-1) obtained in Referential Example 1, 10 ml of ethyl acetate, 10 ml of tetrahydrofuran and 0.15 g of 5% palladium-carbon are reduced at 30°–35° C. under a hydrogen pressure of 5 kg/cm$^2$ for 3 hours. After completion of the reaction, the catalyst is filtered off and the filtrate is concentrated to obtain 1.9 g (yield 99%) of 2-(4-(6-acetoxy-1-heptyl)phenyl)-5-decyloxypyrimidine (XII-31), mp 78°–79° C.

Then, 1.4 g (3 mmol) of (XII-31), 70 ml of 1M phosphate buffer and 0.3 g of Genus Pseudomonas lipase (Amano PS) are vigorously stirred at 30° C. for 40 hours. After completion of the reaction, the reaction mixture is extracted with ethyl acetate and the organic layer is concentrated and purified by chromatography to obtain 0.6 g (yield 46%) of (−)-2-{4-(6-hydroxy-1-heptyl)phenyl}-5-decyloxypyrimidine (V-31), $[\alpha]_D^{20}$=−3.3° (c=1, chloroform).

EXAMPLE 55

A four-necked flask equipped with a stirring device and a thermometer was charged with 7.8 g (0.02 mol) of 2-(4-bromophenyl)-5-decyloxypyrimidine (VI-55), 3.4 g (0.03 mol) of optically active 1-heptyn-3-ol (VII*-55), 0.15 g of bis(triphenylphosphine)-palladium chloride, 0.15 g of copper iodide, 0.28 g of triphenylphosphine and 50 ml of triethylamine. Under a stream of nitrogen gas, the content of the flask was reacted at 80°–90° C. for 7 hours. After completion of the reaction, the reaction mixture was poured into 200 ml of water and extracted with 200 ml of toluene. The toluene layer thus obtained was washed with 3% HCl solution and water and then concentrated under reduced pressure to obtain a brown colored residue.

Purification of the residue by silica gel column chromatography using toluene-ethyl sulfate as eluent gave 6.7 g (yield 79%) of optically active (−)-2-(4-(6-hydroxy-1-heptynyl)phenyl)-5-decyloxypyrimidine (I'-55), mp 82°–83° C. $[\alpha]_D^{20}$=−3.6° (c=1, chloroform).

EXAMPLE 56

A mixed solution consisting of 0.84 g (2 mmol) of optically active 2-(4-(6-hydroxy-1-heptynyl)phenyl)-5-decyloxypyrimidine (I'-55) obtained in Example 55, 3 ml of methanol, 10 ml of THF and 0.1 g of 5% palladium-carbon was hydrogenated under a hydrogen pressure of 3 kg/cm$^2$ at 25°–30° C. The reaction was completed in 2 hours. By filtering off the catalyst and purifying the filtrate by chromatography, 0.83 g (yield 98%) of optically active 2-(4-(6-hydroxy-1-heptyl)phenyl)-5-decyloxypyrimidine (II'-2) was obtained, $[\alpha]_D^{20}$=−3.0° (c=1, chloroform).

EXAMPLE 57

A four-necked flask equipped with a stirring device and a thermometer was charged with 7.3 g (0.02 mol) of 2-(4-bromophenyl)-5-octyloxypyrimidine (VI-57), 6.2 g (0.04 mol) of (+)6-acetoxy-1-heptyne (VII*-57), 0.15 g of bis-(triphenylphosphine)-palladium chloride, 0.15 g of copper iodide, 0.29 g of triphenylphosphine and 50 ml of diethylamine. The content of the flask was reacted under reflux for 9 hours under a stream of nitrogen gas.

After completion of the reaction, work-up treatment and purification were carried out in the same manner as in Example 55 to obtain 6.8 g (yield 78%) of (+)2-(4-(6-acetoxy-1-heptynyl)phenyl)-5-octyloxypyrimidine (I'-57), mp 58°–59° C., $[\alpha]_D^{20}$=+1.5 (c=1, chloroform).

EXAMPLE 58

A mixed solution consisting of 4.4 g (0.01 mol) of (+)2-(4-(6-acetoxy-1-heptynyl)-5-octyloxypyrimidine (I'-57), 40 ml of ethyl acetate and 0.46 g of 5% palladium-carbon was hydrogenated under normal pressure at 20°–25° C. By filtering off the catalyst and concentrating the filtrate, 4.4 g (yield 99%) of (+)2-(4-(6-acetoxy-1-heptyl)phenyl)-5-octyloxypyrimidine was obtained, mp 73°–74° C., $[\alpha]_D^{20}$=+1.3 (c=1, chloroform).

EXAMPLE 59

18.2 g (0.05 mol) of 6-decyloxy-2-bromonaphthalene (VI-59), 10.5 g (0.15 mol) of (+)-3-butyn-2-ol (VII*-59), 0.4 g of copper iodide, 0.7 g of triphenylphosphine, 0.4 g of bis(triphenylphosphine)palladium chloride and 100 ml of diethylamine were stirred under reflux for 12 hours in an atmosphere of nitrogen gas. After completion of the reaction, the reaction mixture was poured into ice/aqueous hydrochloric acid and extracted with 200 ml of ethyl acetate. The organic layer was further washed with water and concentrated under reduced pressure. The residue was purified by silica gel chromatography using toluene-ethyl acetate as eluent to obtain 14.3 g (yield 81%) of optically active (+)-6-decyloxy-2-(3-hydroxy-1-butynyl)naphthalene (I'-59), mp 74°–75° C. $[\alpha]_D^{20}$=+16.9° (c=1, chloroform).

Then, 1.1 g (3 mmol) of optically active 6-decyloxy-2-(3-hydroxy-1-butynyl)naphthalene (I'-59) obtained above, 11 ml of tetrahydrofuran (THF) and 0.11 g of 5% palladium-carbon were hydrogenated under normal pressure. The reaction was completed in 4 hours at 20° C. After filtering off the catalyst, concentration and chromatographic purification gave 1.0 g (yield 98%) of 6-decyloxy-2-(3-hydroxy-1-butyl)naphthalene, $[\alpha]_D^{20}$=−8.7° (c=1, chloroform).

EXAMPLE 60

18.2 g (0.05 mol) of 6-decyloxy-2-bromonaphthalene (VI-60), 15.4 g (0.1 mol) of (+)-2-pentynyloxy-3-butyne (VII*-60), 0.5 g of copper iodide, 0.8 g of triphenylphosphine, 0.4 g of bis(triphenylphosphine)-palladium chloride and 100 ml of triethylamine were stirred under reflux for 7 hours in an atmosphere of nitrogen gas. After completion of the reaction, the reaction mixture was poured into ice-aqueous hydrochloric acid and extracted with 200 ml of ethyl acetate. The organic layer was further washed with water and concentrated under reduced pressure. The residue was purified by silica gel chromatography using toluene-ethyl acetate as eluent to obtain 17.9 g (yield 82%) of optically active (+)-6-decyloxy-2-(3-pentynyloxy-1-butynyl)naphthalene (I'-60), $[\alpha]_D^{20}$=+93 (c=1, chloroform).

In the same manner as above, 1.3 g (3 mmol) of optically active 6-decyloxy-2-(3-pentynyloxy-1-butynyl)naphthalene gave 1.3 g (yield 98%) of 6-decyloxy-2-(3-pentynyloxy-1-butyl)naphthalene, $[\alpha]_D^{20}$=+11.5° (c=1, chloroform).

EXAMPLE 61

A four-necked flask equipped with a stirring device and a thermometer was charged with 20 g (51.1 mmol) of 2-(4-bromophenyl)-5-decyloxypyrimidine (VI-61), 12.9 g (153 mmol) of (−)4-pentyn-2-ol (VII*-61), 0.5 g (1.78 mmol) of copper iodide, 0.67 g (2.55 mmol) of triphenylphosphine, 0.4 g of bis(triphenylphosphine)palladium (II) chloride and 200 ml of triethylamine. The content of the flask was heated and stirred at 90° C. for 8 hours in an atmosphere of nitrogen.

After completion of the reaction, the reaction mixture was poured into 200 ml of water, neutralized with dilute sulfuric acid and extracted with a mixture of toluene and ethyl acetate. The organic solvent layer thus obtained was washed with water and concentrated under reduced pressure to obtain a yellow-brown colored residue.

Purification of the residue by silica gel column chromatography using toluene-ethyl acetate as eluent gave 16.5 g (yield 81%) of (−)5-decyloxy-2-((4-hydroxy-1-pentynyl)phenyl)pyrimidine (I'-61), $[\alpha]_D^{20}$=−7.4 (c=1, chloroform), mp 71°–72° C.

If the (I'-61) obtained herein is reduced in the same manner as in Example 56, the following compound can be synthesized:

5-(decyloxy)-2-((4-hydroxypentyl)phenyl)pyrimidine (II'-61), $[\alpha]_D^{20}$=−3.1 (c=1, chloroform).

EXAMPLE 62

7.8 g (0.02 mol) of 4-decyloxy-4'-bromobiphenyl (VI-62), 4.5 g (0.04 mol) of 5-methoxy-1-hexyne, 0.25 g of bis(triphenylphosphine)-palladium chloride, 0.3 g of copper iodide, 0.45 g of triphenylphosphine, 30 ml of triethylamine and 10 ml of dimethylformamide were charged and reacted at 80° C. for 10 hours under a stream of nitrogen gas.

After completion of the reaction, the reaction mixture was poured into 100 ml of water, ethyl acetate was added thereto, and the whole was weakly acidified with 10% aqueous hydrochloric acid. The organic layer was further washed with water and concentrated under reduced pressure to obtain 6.7 g (yield 82%) of 4-decyloxy-4'-(5-methoxy-1-hexynyl)biphenyl (I'-62), mp 97°–99° C. $[\alpha]_D^{20}$=−3.1 (c=1, chloroform).

EXAMPLE 63

2.1 g (5 mmol) of 4-decyloxy-4'-(5-methoxy-1-hexynyl)biphenyl (I'-62) obtained in Example 62 was dissolved in 20 ml of ethyl acetate and 10 ml of THF, and reduced with hydrogen at 30° C. for 6 hours in the presence of 0.2 g of 5% Pd-carbon. After completion of the reaction, the catalyst was filtered off and the filtrate was concentrated under reduced pressure to obtain 2.1 g (yield 99%) of 4-decyloxy-4'-(5-methoxy-1-hexyl)biphenyl (II'-62), $[\alpha]_D^{20}$=−2.5° (c=1, chloroform).

EXAMPLE 64

7.5 g (0.02 mol) of 3-decyl-6-bromobiphenylpyridazine (VI-64), 3.8 g (0.03 mol) of (+)4-acetoxy-1-pentyne, 0.2 g of bis(triphenylphosphine)-palladium chloride, 0.2 g of copper iodide, 0.3 g of triphenylphosphine, 20 ml of diethylamine and 20 ml of N-methylpyrrolidone were charged and reacted under reflux for 10 hours.

After completion of the reaction, work-up treatment and purification were carried out in the same manner as in Example 1 to obtain 7.0 g (yield 83%) of (+)-3-decyl-6-(4-acetoxy-1-pentynyl)phenylpyridazine (I'-64), $[\alpha]_D^{20}$=13.0 (c=1, chloroform).

Then, 4.2 g (0.01 mol) of (I'-64) obtained above, 20 ml of methanol, 20 ml of ethyl acetate and 0.1 g of 2% platinum-carbon were reduced at a hydrogen pressure of 10 kg/cm² at 25°–30° C.

After completion of the reaction, the catalyst was filtered off and the filtrate was concentrated to obtain 4.2 g (yield 99%) of optically active 3-decyl-6-(4-acetoxy-1-pentyl)phenylpyridazine, mp 68°–69° C., $[\alpha]_D^{20}$=−11.8° (c=1, chloroform).

EXAMPLES 65–76

The optically active acetylene alcohol derivatives (I') and optically active saturated alcohols (II') shown in Table 10 can be obtained by successively repeating the reaction and work-up treatment of Example 55, except that the starting materials shown in Table 10 are used.

TABLE 10

| Example | Starting material | | | | Conditions |
|---|---|---|---|---|---|
| | Halide (VI) | | Acetylene (VII*) | | |
| 65 | C$_8$H$_{17}$O—⟨phenyl⟩—⟨pyrimidine(N,N)⟩—Br | (7.3 g) | (−)-6-Hydroxy-1-heptyne (−11.5°) | (3.5 g) | Example 57 |
| 66 | " | " | (−)-6-Ethoxy-1-heptyne (−10.0°) | (4.2 g) | " |
| 67 | " | " | (−)-6-Ethoxypropoxy-1-heptyne (−8°) | (6 g) | " |
| 68 | C$_{10}$H$_{21}$O—⟨phenyl⟩—⟨pyrimidine(N,N)⟩—Br | (7.8 g) | (−)-2-Hexyloxy-5-hexyne (−4.0°) | (5.4 g) | " |
| 69 | C$_{10}$H$_{21}$O—⟨pyrimidine(N,N)⟩—⟨phenyl⟩—Br | (7.8 g) | (−)≡⟨CH(CH$_3$)*⟩—O—CO—CH=CH— | (−13°) 4.8 g | " |

TABLE 10-continued

| Example | | | | | | | | |
|---|---|---|---|---|---|---|---|---|
| 70 | C₁₀H₂₁—[pyridine]—[phenyl]—Br | (7.5 g) | (−)≡—CH(CH₃)—*OCOC₈H₁₇ | | | | (−9°) 5.2 g | " |

| | Optically active acetylene alcohol derivative (I') | | | | | | Yield | $[\alpha]_D^{20}$ (c = 1, |
|---|---|---|---|---|---|---|---|---|
| | $R^1$ | m | —A—B— | n | s | $R_0^2$ | (%) | Chloroform) |
| 65 | C₈H₁₇ | 1 | 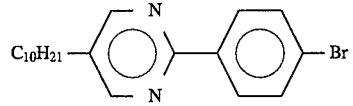 pyridine-phenyl | 3 | 0 | H | 81 | −3.8° |
| 66 | " | 1 | " | 3 | 0 | C₂H₅ | 79 | −3.4° |
| 67 | " | 1 | " | 3 | 0 | C₂H₅OC₃H₆— | 80 | −3.1° |
| 68 | C₁₀H₂₁ | 1 | 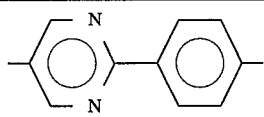 phenyl-pyridine | 2 | 0 | C₆H₁₃ | 76 | −2.8° |
| 69 | " | 1 | 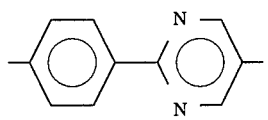 pyridine-phenyl | 1 | 1 | —CH=CH—CH₃ | 55 | −2.8° |
| 70 | " | 0 | " | 1 | 1 | C₈H₁₇ | 75 | −2.4° |

| | Optically active saturated alcohol (II") | | | | | | Condi- | Yield | $[\alpha]_D^{20}$ (c = 1, |
|---|---|---|---|---|---|---|---|---|---|
| | $R^1$ | m | —A—B— | n | s | $R_0^2$ | tions | (%) | Chloroform) |
| 65 | C₈H₁₇ | 1 | 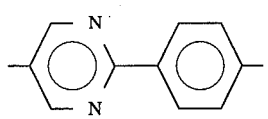 pyridine-phenyl | 3 | 0 | H | Example 58 | 98 | −3.6° |
| 66 | " | 1 | " | 3 | 0 | C₂H₅ | " | 98 | −3.1° |
| 67 | " | 1 | " | 3 | 0 | C₂H₅OC₃H₆ | " | 97 | −2.9° |
| 68 | C₁₀H₂₁ | 1 | 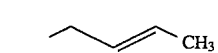 phenyl-pyridine | 2 | 0 | C₆H₁₃ | " | 98 | −2.7° |
| 69 | " | 1 | 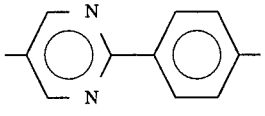 pyridine-phenyl | 1 | 1 | C₄H₉ | " | 98.5 | −2.5° |
| 70 | " | 0 | " | 1 | 1 | C₈H₁₇ | " | 98 | −2.3° |

| | Starting material | | | | |
|---|---|---|---|---|---|
| | Halide (VI) | | Acetylene (VII*) | | Conditions |
| 65 | C₈H₁₇O—[phenyl]—[phenyl]—Br 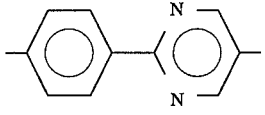 | (7.3 g) | (−)-6-Hydroxy-1-heptyne (−11.5°) | (3.5 g) | Example 57 |
| 66 | " | | (−)-6-Ethoxy-1-heptyne (−10.0°) | (4.2 g) | " |
| 67 | " | | (−)-6-Ethoxypropoxy-1-heptyne (−8°) | (6 g) | " |

TABLE 10-continued

| Example | | | | | | | | | |
|---|---|---|---|---|---|---|---|---|---|
| 68 | 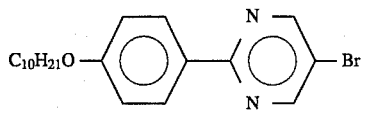 C₁₀H₂₁O—⟨phenyl⟩—⟨pyrimidine⟩—Br | (7.8 g) | (−)-2-Hexyloxy-5-hexyne | (5.4 g) | (−4.0°) | | | | " |
| 69 | 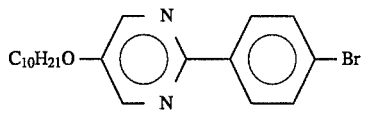 C₁₀H₂₁O—⟨pyrimidine⟩—⟨phenyl⟩—Br | (7.8 g) | (−)≡—CH₂—*CH(CH₃)—O—CO—CH=CH— | 4.8 g | (−13°) | | | | " |
| 70 | 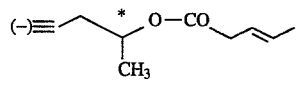 C₁₀H₂₁—⟨pyridazine⟩—⟨phenyl⟩—Br | (7.5 g) | (−)≡—CH₂—*CH(CH₃)—OCOC₈H₁₇ | 5.2 g | (−9°) | | | | " |

| | Optically active acetylene alcohol derivative (I″) | | | | | | Yield | $[\alpha]_D^{20}$ (c = 1, |
|---|---|---|---|---|---|---|---|---|
| | $R^1$ | m | —A—B— | n | s | $R_o^2$ | (%) | Chloroform) |
| 71 | C₁₆H₃₃ | 1 | 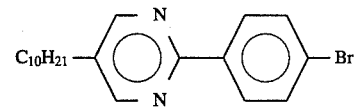 | 3 | 1 | 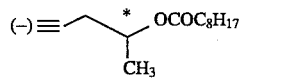 —C≡C—CH₃ | 73 | −2.5° (mp 52–53° C.) |
| 72 | C₁₀H₂₁ | 1 | 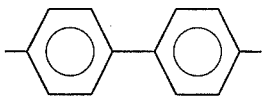 | 3 | 0 | H | 83 | −3.0° |
| 73 | " | 1 | " | 3 | 1 | 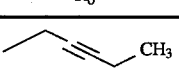 *CH(Cl)CH₃ | 85 | |
| 74 | " | 1 | " | 3 | 0 | 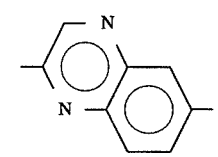 —CH₂—*CH(CH₃)C₂H₅ | 80 | |
| 75 | " | 1 | 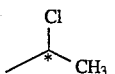 | 1 | 1 | C₃H₇ | 81 | −3.2° |
| 76 | " | 1 | 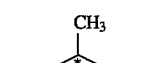 | 1 | 0 | H | 82 | −3.4° |

| | Optically active saturated alcohol (II″) | | | | | | Condi- | Yield | $[\alpha]_D^{20}$ (c = 1, |
|---|---|---|---|---|---|---|---|---|---|
| | $R^1$ | m | —A—B— | n | s | $R_o^2$ | tions | (%) | Chloroform) |
| 71 | C₁₆H₃₃ | 1 | 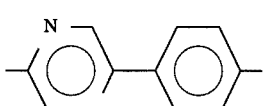 | 3 | 1 | C₅H₁₁ | Example 58 | 98 | −2.4° (mp 52–53° C.) |
| 72 | C₁₀H₂₁ | 1 | 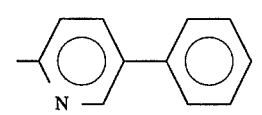 | " | 0 | H | " | 98 | −2.8° |
| 73 | " | " | " | " | 1 | 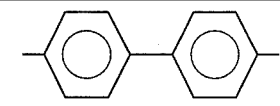 *CH(Cl)CH₃ | " | 75 | |

TABLE 10-continued

| Example | | | | | | | | | |
|---|---|---|---|---|---|---|---|---|---|
| 74 | " | " | " | " | 0 | 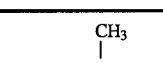 | " | 98 | |
| 75 | " | " |  | 1 | 1 | $C_3H_7$ | " | 98 | −3.0° |
| 76 | " | " |  | 3 | 0 | H | " | 98 | −3.2° |

We claim:

1. An acetylene derivative represented by the formula (I):

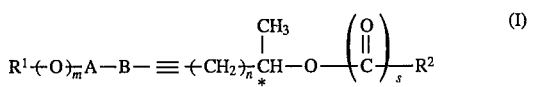

wherein $R^1$ represents a $C_3$–$C_{20}$ alkyl group, a $C_3$–$C_{20}$ haloalkyl group, a $C_3$–$C_{20}$ alkenyl group, a $C_3$–$C_{20}$ alkynyl group of a $C_3$–$C_{20}$ carbocyclic group, $R_2$ represents a $C_1$–$C_{20}$ alkyl group, a $C_1$–$C_{20}$ haloalkyl group, a carbocyclic group having carbon atoms up to 20, an alkoxyalkyl group having 2–20 atoms, an alkenyl group having carbon atoms up to 20, or an alkynyl group having carbon atoms up to 20, A and B each represents

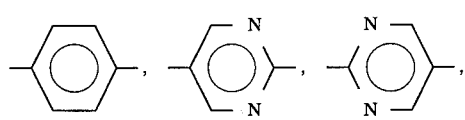

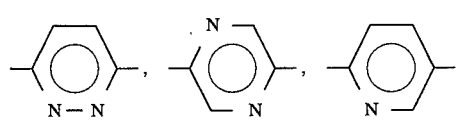

or

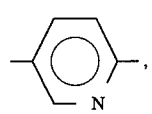

m and s each represents 0 or 1, n represents an integer of 0–6, and the mark * means asymmetric carbon atom.

2. A liquid crystal composition characterized by containing at least one compound represented by formula (I):

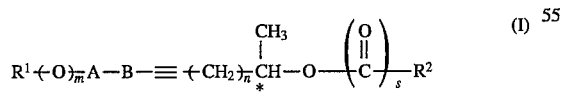

wherein $R^1$ represents saturated or unsaturated alkyl group having 3–20 carbon atoms, $R^2$ represents saturated or unsaturated alkyl group having 1–20 carbon atoms which may optionally be substituted by halogen atom or alkoxyalkyl group having 2–20 carbon atoms, A and B each represents

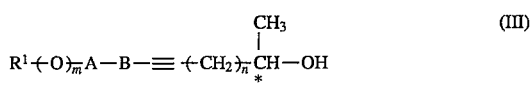

m and s each represents 0 or 1, n represents an integer of 0–6, and the mark * means asymmetric carbon atom, as ingredient.

3. An optically active alcohol derivative represented by general formula (III):

$$R^1\mathrm{+O)}_{\overline{m}}A\mathrm{-B-}\equiv\mathrm{+CH}_2)_{\overline{n}}\underset{*}{\mathrm{CH}}\mathrm{-OH} \quad (\mathrm{III})$$

wherein $R^1$ represents saturated or unsaturated alkyl group having 3–20 carbon atoms, m represents 0 or 1, n represents an integer of 0–6, A and B each represents

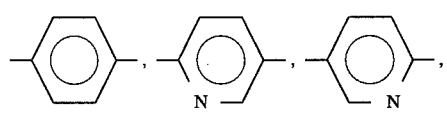

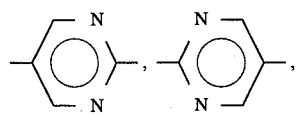

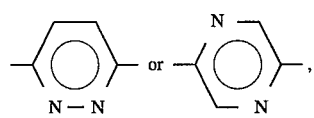

and the mark * means asymmetric carbon atom.

* * * * *